United States Patent
Klasovsky et al.

(10) Patent No.: US 9,567,276 B2
(45) Date of Patent: Feb. 14, 2017

(54) CHROMIUM-FREE HYDROGENATION OF HYDROFORMYLATION MIXTURES

(71) Applicant: Evonik Degussa GmbH, Essen (DE)

(72) Inventors: Florian Klasovsky, Haltern am See (DE); Robert Franke, Marl (DE); Marc Becker, Dortmund (DE); Thomas Quandt, Marl (DE); Frank Geilen, Haltern am See (DE)

(73) Assignee: Evonik Degussa GmbH, Essen (DE)

(*) Notice: Subject to any disclaimer, the term of this patent is extended or adjusted under 35 U.S.C. 154(b) by 0 days.

(21) Appl. No.: 14/978,579

(22) Filed: Dec. 22, 2015

(65) Prior Publication Data
US 2016/0176792 A1    Jun. 23, 2016

(30) Foreign Application Priority Data
Dec. 23, 2014 (EP) .................................. 14199938

(51) Int. Cl.
*C07C 29/141* (2006.01)
*B01J 37/02* (2006.01)
*B01J 37/08* (2006.01)
*B01J 37/18* (2006.01)
*B01J 23/755* (2006.01)

(52) U.S. Cl.
CPC ............ *C07C 29/141* (2013.01); *B01J 23/755* (2013.01); *B01J 37/0201* (2013.01); *B01J 37/0236* (2013.01); *B01J 37/08* (2013.01); *B01J 37/18* (2013.01)

(58) Field of Classification Search
CPC .............................. C07C 29/141; B01J 23/00
USPC ..................... 568/881, 882, 883; 502/330
See application file for complete search history.

(56) References Cited

U.S. PATENT DOCUMENTS

| | | |
|---|---|---|
| 4,762,817 A | 8/1988 | Logsdon et al. |
| 5,093,534 A | 3/1992 | Ludwig et al. |
| 6,239,318 B1 * | 5/2001 | Schuler ............... C07C 29/141 568/881 |
| 6,680,414 B2 * | 1/2004 | Knoop ................. C07C 29/141 568/830 |
| 7,524,997 B2 * | 4/2009 | Kaizik .................. B01J 23/755 568/883 |
| 2010/0243530 A1 | 9/2010 | Marchand et al. |
| 2011/0060169 A1 | 3/2011 | Kaizik et al. |
| 2012/0253083 A1 | 10/2012 | Kaizik et al. |

FOREIGN PATENT DOCUMENTS

| | | |
|---|---|---|
| CN | 102247856 | 11/2011 |
| CN | 103894207 | 7/2014 |
| DE | 32 28 881 | 2/1984 |
| DE | 10 2008 007 080 | 8/2009 |
| GB | 1 579 159 | 11/1980 |
| PL | 161223 | 6/1993 |
| WO | WO 2006/079850 A1 | 8/2006 |
| WO | WO 2009/146988 A2 | 12/2009 |

OTHER PUBLICATIONS

Ananthan, S.A., et al., "Liquid Phase Selective Hydrogenation of Citral Bimetallic Transition Metal Catalysts," *International Journal of Chemistry* 3(2):55-66 (Jun. 2011).
Singaporean Written Opinion for counterpart Singapore application 10201510496U filed Dec. 21, 2015.

* cited by examiner

*Primary Examiner* — Sikarl Witherspoon
(74) *Attorney, Agent, or Firm* — Law Offices of Michael A. Sanzo, LLC (57) ABSTRACT

The invention relates to a process for the preparation of alcohols by hydrogenation of aldehydes, in which use mixture comprising at least one aldehyde and at least one accompanying component is brought into contact, in the presence of hydrogen, with a heterogeneous catalyst, giving a product mixture which comprises at least the alcohol corresponding to the hydrogenated aldehyde, and at least one by-product, where the catalyst comprises a support material, and nickel and copper applied thereto. The invention also includes a chromium-free catalyst suitable for hydrogenating aldehyde mixtures with different chain lengths, in particular those which originate from different hydroformylations and can also comprise substances with C=C double bonds.

20 Claims, 1 Drawing Sheet

CHROMIUM-FREE HYDROGENATION OF HYDROFORMYLATION MIXTURES

CROSS REFERENCE TO RELATED APPLICATIONS

The present application claims priority to European Application, EP 14199938.3, filed on Dec. 23, 2014, the contents of which is incorporated herein by reference in its entirety.

FIELD OF THE INVENTION

The invention relates to a process for the preparation of alcohols by hydrogenation of aldehydes, in which a use mixture comprising at least one aldehyde and at least one accompanying component is brought into contact, in the presence of hydrogen, with a heterogeneous catalyst, giving a product mixture which comprises at least the alcohol corresponding to the hydrogenated aldehyde, and at least one by-product, where the catalyst comprises a support material, and nickel and copper are applied thereto. In addition, the invention relates to the preparation of the associated catalyst and its use in the process.

BACKGROUND OF THE INVENTION

The elimination of hydrogen (dehydrogenation) from an alcohol gives an aldehyde. Conversely, alcohols can be prepared from aldehydes by hydrogenation (addition of hydrogen). Hydrogenation in general is a reaction carried out very frequently in industrial technology. But also specifically the hydrogenation of aldehydes is practised on an industrial scale, namely in the production of so-called oxo alcohols.

Oxo alcohols are alcohols which are produced in the course of hydroformylation (oxo reaction). During the hydroformylation, an olefin (alkene) is reacted with a synthesis gas (this is a mixture of carbon monoxide and hydrogen) to give an aldehyde. Subsequent hydrogenation gives the actual oxo alcohol. Oxo alcohols serve as intermediates for producing surfactants and/or plasticizers for plastic. Worldwide, several million tons of oxo alcohols are produced every year. Since the hydrogenation of the aldehydes obtained by the hydroformylation is a necessary step in the production of oxo alcohols, the present invention deals with a process that is of relevance on an industrial scale.

In industrial practice, oxo aldehydes are generally hydrogenated in the liquid phase on heterogeneous fixed-bed catalysts. On account of the large throughput amounts, the catalyst is attributed the decisive importance for the process since it determines the reaction rate and also the selectivity of the hydrogenation. The selection of a suitable catalyst is not trivial since the aldehydes to be hydrogenated never occur in pure form, but as a mixture of structural isomeric aldehydes which is always accompanied by a large number of troublesome accompanying components which firstly bring about secondary reactions undesired in the hydrogenation and secondly damage the hydrogenation catalyst. Since the composition of the use mixture comprising the aldehydes to be hydrogenated is determined by the upstream hydroformylation, the hydrogenation catalyst has to be precisely adapted to the particular hydroformylation.

For the hydrogenation of oxo aldehydes, catalysts that have proven useful are those which comprise a support material on which copper, chromium and nickel are applied as active components.

A corresponding catalyst is disclosed in DE19842370A1. It comprises copper and nickel, in each case in a concentration range from 0.3 to 15% by weight and chromium in a weight fraction of from 0.05% by weight to 3.5% by weight. The support material used is porous silicon dioxide or aluminium oxide.

EP1219584B1 reveals that such a catalyst also manages with the accompanying component water, which is to be expected in particular during the co-catalysed hydroformylation. Water is critical since it can have a lasting negative influence on the surface structure of the catalyst by, for example, reducing the specific surface area. For this reason, the aldehyde mixtures originating from the cobalt-catalysed hydroformylation are particularly demanding to hydrogenate.

A further development of this Ni/Cu/Cr catalyst consists in adding barium to the support material (EP2180947B1).

WO2009/146988A1 deals with the two-stage hydrogenation of oxo alcohols over two different Ni/Cu/Cr catalysts.

Although the nickel/copper/chromium catalysts have proven useful in the industrially practised hydrogenation of oxo aldehydes, there is still the need for an alternative. The reason for this is the chromium present.

According to Annex XIV of the REACH regulation, chromium-containing substances such as the catalysts described above may only be used in the European Union after authorization by the Commission. The granting of authorization is associated with great complexity and high costs; moreover, granting of authorization cannot be expected a priori. Moreover, the application procedure has to be repeated every five years.

The reason for these strict conditions is the undisputed carcinogenicity of the chromium(IV) compounds present in the catalyst. These are firstly relevant when hydrogenation catalyst has to be disposed of following deactivation and, secondly, when it is newly produced by impregnation with alkali metal chromates or alkali metal dichromates.

For health and cost reasons there is therefore a great need for a chromium-free alternative to the hydrogenation of oxo aldehydes.

Chromium-free hydrogenation catalysts are disclosed in EP1749572A1. The support material used is porous aluminium oxide and the hydrogenation-active components are nickel or cobalt. The examples reveal that a $Ni/Al_2O_3$ or a $Co/Al_2O_3$ system is suitable for the hydrogenation of oxo aldehydes; the properties and productivity of these systems, however, has not been investigated. The disadvantage of the cobalt catalysts shown in EP1749572A1 consists in the fact that they in any case have to be reduced at relatively high temperatures of 350° C. to 450° C. This usually does not take place in-situ in the reactor since the reactors for the aldehyde hydrogenation are designed only for a temperature of up to about 200° C. Consequently, the cobalt catalysts have to be reduced ex situ and then be incorporated into the hydrogenation reactor under a protective atmosphere. This is very complex. Moreover, cobalt is a comparatively expensive material.

For the nickel catalysts, approx. 200° C. could just suffice for an in situ reaction. However, EP1749572A1 mentions that the $Ni/Al_2O_3$ system favours the further reaction and the reaction must therefore be ended very quickly. That is not always easy to accomplish in industrial use. The chromium-free hydrogenation catalysts shown in EP1749572A1 have overall so many disadvantages that they are not real alternatives to the classic Ni/Cu/Cr systems.

DE3737277C2 discloses a chromium-free catalyst for the hydrogenation of aldehydes which is based on copper/zinc oxides. Potassium, nickel and/or cobalt and additionally an alkali metal are present as further hydrogenation-active metals. This system is a so-called uniform-composition catalyst which consists exclusively of the hydrogenation-active materials. Such uniform-composition catalysts are very expensive to produce and are therefore too costly for industrial use. After all of this, it has hitherto not been possible to find a chromium-free catalyst which is suitable for the hydrogenation of hydroformylation mixtures on an industrial scale and which can be produced easily.

DESCRIPTION OF THE INVENTION

The object of the invention therefore consists in indicating such a catalyst. In particular, the same catalyst should be suitable for hydrogenating aldehyde mixtures with different chain lengths, in particular those which originate from different hydroformylations and can also comprise substances with C=C double bonds.

Surprisingly, this object was achieved by omitting the chromium during the preparation of a classic Cu/Ni/Cr system, such that a catalyst is obtained on whose support material only copper and nickel occur as hydrogenation-active components, but not chromium.

This finding is surprising since in the past it has always been assumed that chromium is a necessary component for such hydrogenation tasks. In fact, long-term experiments demonstrate that although a small chromium content of 0.05% by weight to 3.5% by weight offers definite advantages in the start-up range, over the long term the performance of chromium-free and chromium-containing Cu/Ni systems is approximately the same. For this reason, there are no longer any concerns against using chromium-free Cu/Ni systems in the hydrogenation of hydroformylation mixtures. Consequently, the invention provides a process for the preparation of alcohols by hydrogenation of aldehydes, in which a use mixture comprising at least one aldehyde, and at least one accompanying component is brought into contact, in the presence of hydrogen, with a heterogeneous catalyst, giving a product mixture which comprises at least the alcohol corresponding to the hydrogenated aldehyde, and at least one by-product, where the catalyst comprises a support material, and nickel and copper applied thereto, where the catalyst in activated form has the following composition adding up to 100% by weight:
support material: from 85% by weight to 95% by weight, preferably from 88% by weight to 92% by weight;
copper: from 5.3% by weight to 8.4% by weight, preferably from 6.5% by weight to 7.0% by weight;
nickel: from 2.2% by weight to 3.9% by weight, preferably from 2.8% by weight to 3.3% by weight;
chromium: less than 50 ppm by weight, preferably less than 5 ppm by weight;
others: less than 1% by weight.

Such a catalyst can be referred to as chromium-free. In this connection, "free from chromium" means that no chromium was actively used during the preparation of the catalyst, in particular that the support material has not been impregnated with chromium-containing substances. As chromium-containing substances, compounds comprising Cr-III and Cr-VI are especially noteworthy. On account of the analysis possibilities nowadays, it cannot be excluded that traces of chromium will be detected in the catalyst according to the invention. These could originate, for example, from the steel of the apparatuses with which the catalyst comes into contact during its preparation, its storage, its transportation, its incorporation or its use. However, this is not desired chromium content.

Insofar as freedom from chromium according to the invention should be defined with a numerical value, then a catalyst which, based on its total weight, comprises less than 50 ppm by weight of chromium is considered to be "chromium-free" in the context of this invention. Preferably, the catalyst even comprises less than 5 ppm by weight of chromium. The measurement unit ppm is understood here as $10^{-6}$. The stated limiting values for chromium refer in particular to the total content of substances which comprise Cr-III and Cr-VI.

Compared to the catalyst known from DE19842370A1, which comprises at least 0.05% by weight (corresponding to 500 ppm) of chromium, the chromium content of a catalyst according to the invention is one to two orders of magnitude less.

By dispensing with an impregnation of the support material with alkali metal chromates or alkali metal dichromates during the preparation of the catalyst, it is possible to ensure the required freedom from chromium.

Suitable support materials are in principle those substances which exhibit inert behaviour (i.e. do not co-react) in the hydrogenation and are capable of supporting the catalytically active substances nickel and copper. Different from a uniform-composition catalyst, the support catalyst described here consequently comprises the inert support material on which the active material is applied. Suitable support materials are commercially available and can be coated with the active materials on an industrial scale with the help of proven technology. The support material is preferably aluminium oxide or silicon dioxide, or it is a mixture of aluminium oxide and silicon dioxide (silica/alumina).

The support material should be porous. The specific pore volume of the support material should be between 0.5 ml/g and 0.9 ml/g. The value of the specific pore volume is determined by the cyclohexane immersion method. For this, a sample of the support material is placed into a vessel and the vessel is evacuated. The sample in the air-free vessel is weighed. Then, the vessel is flooded with an amount of cyclohexane, measured volumetrically beforehand, such that the sample is impregnated in it. The cyclohexane is allowed to penetrate into the sample. Then, the cyclohexane is shaken off and the amount shaken off is measured volumetrically. The difference compared to the amount of cyclohexane poured in corresponds to the amount that has penetrated into the pores, i.e. the pore volume. This pore volume is then related to the weight of the sample. This gives the specific pore volume of the support.

The specific surface area of the support material (BET surface area) should be between 240 $m^2/g$ to 280 $m^2/g$. The specific surface area is determined by ISO method 9277.

The hydrogenation should be carried out at a pressure between $15*10^5$ Pa and $25*10^5$ Pa and at a temperature between 140° C. and 180° C., pressure and temperature being selected such that use mixture and product mixture are present in a liquid phase. This increases the process intensity. The hydrogen should be present in the hydrogenation in a superstoichiometric amount in order to permit complete hydrogenation. However, the concentration of the hydrogen should be selected such that at least some of the hydrogen is present dissolved in the liquid phase. As a result, the flow dynamic is not so greatly adversely affected by gas bubbles.

According to the invention, oxo aldehydes are hydrogenated to the corresponding alcohols. Consequently, the use mixture originates from a hydroformylation and as such has a plurality of aldehydes with the same number n of carbon atoms, and corresponding alcohols and high boilers, where n is a natural number between three and eighteen.

Preferably, the use mixture has one of the following specifications A to E, with the specified compositions in each case adding up to 100% by weight:

Specification A:
total fraction of the aldehydes having five carbon atoms: 80% by weight to 100% by weight;
total fraction of the alcohols having five carbon atoms: 0% by weight to 1% by weight;
total fraction of other hydrocarbons: 2% by weight to 20% by weight.

Specification B:
total fraction of the aldehydes having nine carbon atoms: 25% by weight to 75% by weight;
total fraction of the alcohols having nine carbon atoms: 10% by weight to 55% by weight;
total fraction of acetals: 0.5% by weight to 5.5% by weight;
total fraction of further hydrocarbons: 0% by weight to 40% by weight;
water: 0% by weight to 3% by weight.

Specification C:
total fraction of the aldehydes having nine carbon atoms: 15% by weight to 65% by weight;
total fraction of the alcohols having nine carbon atoms; 20% by weight to 65% by weight;
total fraction of acetals: 0.5% by weight to 5.5% by weight;
total fraction of further hydrocarbons: 0% by weight to 40% by weight;
water: 0% by weight to 1% by weight.

Specification D:
total fraction of the aldehydes having ten carbon atoms: 50% by weight to 100% by weight;
total fraction of the alcohols having ten carbon atoms: 0% by weight to 40% by weight;
total fraction of further hydrocarbons: 0% by weight to 5% by weight;
fraction of water: 0.5% by weight to 5% by weight.

Specification E:
total fraction of the aldehydes having thirteen carbon atoms: 60% by weight to 85% by weight;
total fraction of the alcohols having thirteen carbon atoms: 1% by weight to 20% by weight;
total fraction of further hydrocarbons: 10% by weight to 40% by weight;
fraction of water: 0.1% by weight to 1% by weight.

A particular advantage of the catalyst consists in the fact that it is also suitable for mixed hydrogenation, i.e. can process a use mixture which is composed of two or more different hydroformylation discharges. Thus, at sites where at least two hydroformylations are operated in parallel, it is possible to combine the hydroformylation mixtures of both oxo plants and to hydrogenate them in a hydrogenation process over the catalyst found here. This saves capital costs for the hydrogenation plant. If the first oxo plant produces for example aldehydes having n carbon atoms and the second oxo plant produces aldehydes having m carbon atoms, then the combined use mixture for the hydrogenation comprises a plurality of aldehydes with the same number n of carbon atoms and a plurality of aldehydes with the same number m of carbon atoms, and also in each corresponding alcohols and high boilers, where n and m are different natural numbers between three and eighteen. The hydrogenation of such a use mixture originating from at least two different hydroformylations is particularly preferred.

The chromium-free catalyst used according to the invention is prepared as follows:
a) provision of a support material;
b) impregnation of the support material with a chromium-free solution of copper(II) hydroxide carbonate, nickel hydroxycarbonate paste, ammonium carbonate, ammonia and water;
c) drying of the impregnated support material in the stream of air at temperatures below 100° C.;
d) calcinations of the dried, impregnated support material in the stream of air at temperatures below 450° C.;
e) activation of the calcined, dried, impregnated support material by reduction with hydrogen to give the active catalyst, where the activation takes place in situ or ex situ.

Such a preparation process is likewise part of the invention since the catalyst used according to the invention attains its freedom from chromium by virtue of this procedure, more precisely by virtue of the chromium-free impregnation.

The use of a catalyst prepared in this way in a process for the hydrogenation of aldehydes is thus likewise provided by the invention.

BRIEF DESCRIPTION OF THE DRAWINGS

FIG. 1.

FIG. 2.

The invention will now be explained in more detail by reference to examples.

EXAMPLES

Example 0

A moulded porous aluminium oxide support (extrudates with a diameter of about 1.2 mm, a BET surface area of about 260 m$^2$/g and a pore volume of about 0.7 ml/g) is impregnated with an ammoniacal aqueous solution containing nickel and copper compounds. The aqueous impregnation solution is obtained from copper(II) hydroxide carbonate, nickel hydroxycarbonate paste, ammonium carbonate, aqueous ammonia solution and water. The impregnation can take place by various customary methods, e.g. spray impregnation, vacuum impregnation or steeping at atmospheric pressure. The impregnation can take place such that the amount of solution is chosen such that the pores are filled partly or completely with impregnation solution or the support is impregnated in an excess of solution. After the impregnation, the material is dried in the stream of air (at temperatures below 100° C.). The dried precursor is then calcined in the stream of air (at temperatures of 450° C.). Afterwards, nickel and copper are present in oxidic form in the aluminium oxide matrix. After the calcination, the catalyst precursor comprises 6.5-7.0% copper, 2.8-3.3% nickel. The catalyst precursor is only converted to the actual catalytically active form after activation in the reactor, e.g. by a reduction of the oxidic nickel and copper compounds with hydrogen.

Example 1

A reaction discharge from the cobalt-catalysed hydroformylation of dibutene was hydrogenated continuously in a circulation apparatus at 180° C. and 25 bar absolute over 150 g of catalyst in the liquid phase. 0.90 l of starting material were pushed through per hour for a circulation of 24 l/h. The amount of off-gas was 5 l/h (STP). A chromium-free Ni/Cu catalyst on $Al_2O_3$ support material prepared according to Example 0 was used. The composition of the use material used is shown in Table 1.

TABLE 1

Composition of the use mixture comprising C9 aldehydes

| Component | HC[a] | IR[b] | AL[c] | FOR[d] | OL[e] | Ethers[f] | Esters[g] | Acetals[h] | Water | Remainder |
|---|---|---|---|---|---|---|---|---|---|---|
| Content [% by mass] | 5.5 | 0.1 | 69.2 | 0.3 | 21.7 | 0.0 | 0.8 | 1.6 | 0.7 | 0.0 |

[a]HC: Hydrocarbon;
[b]Interim run;
[c]$C_9$-aldehydes;
[d]$C_9$-formates;
[e]C9-alcohols;
[f]$C_9/C_9$-ethers;
[g]$C_9/C_9$-esters;
[h]$C_9$-$C_9$-acetals The composition of the product mixture is shown in Table 2.

TABLE 2

Composition of the product mixture according to Example 1 (data in % by mass)

| t [h] | HC[a] | IR[b] | AL[c] | FOR[d] | OL[e] | Ethers[f] | Esters[g] | Acetals[h] | Remainder |
|---|---|---|---|---|---|---|---|---|---|
| 18 | 5.3 | 0.1 | 2.0 | 0.0 | 89.5 | 0.0 | 0.7 | 2.3 | 0.0 |
| 25 | 5.3 | 0.1 | 2.1 | 0.0 | 90.0 | 0.0 | 0.6 | 1.8 | 0.1 |
| 42 | 5.2 | 0.1 | 2.2 | 0.0 | 89.8 | 0.0 | 0.6 | 1.9 | 0.1 |
| 49 | 5.3 | 0.1 | 2.3 | 0.0 | 89.6 | 0.0 | 0.6 | 1.9 | 0.1 |
| 66 | 5.3 | 0.1 | 2.3 | 0.0 | 89.4 | 0.0 | 0.6 | 2.0 | 0.1 |
| 73 | 5.2 | 0.1 | 2.4 | 0.0 | 89.5 | 0.0 | 0.6 | 2.0 | 0.1 |
| 89 | 5.4 | 0.1 | 2.6 | 0.0 | 89.1 | 0.0 | 0.6 | 2.1 | 0.1 |
| 97 | 5.4 | 0.1 | 2.5 | 0.0 | 89.0 | 0.0 | 0.6 | 2.2 | 0.1 |
| 162 | 5.4 | 0.1 | 2.8 | 0.0 | 88.6 | 0.0 | 0.6 | 2.4 | 0.1 |
| 169 | 5.4 | 0.1 | 2.8 | 0.0 | 88.6 | 0.0 | 0.6 | 2.3 | 0.1 |
| 186 | 5.4 | 0.1 | 2.7 | 0.0 | 89.3 | 0.0 | 0.6 | 1.9 | 0.1 |
| 193 | 5.4 | 0.1 | 2.8 | 0.0 | 89.1 | 0.0 | 0.6 | 1.9 | 0.1 |
| 210 | 5.4 | 0.1 | 2.8 | 0.0 | 89.0 | 0.0 | 0.6 | 2.0 | 0.1 |
| 217 | 5.4 | 0.1 | 2.9 | 0.0 | 89.0 | 0.0 | 0.6 | 1.9 | 0.1 |
| 234 | 5.3 | 0.1 | 3.0 | 0.0 | 88.8 | 0.0 | 0.6 | 2.0 | 0.1 |
| 241 | 5.3 | 0.1 | 3.0 | 0.0 | 88.9 | 0.0 | 0.6 | 2.0 | 0.1 |
| 258 | 5.4 | 0.1 | 3.1 | 0.0 | 88.7 | 0.0 | 0.6 | 2.0 | 0.1 |
| 265 | 5.4 | 0.1 | 3.0 | 0.0 | 88.6 | 0.0 | 0.6 | 2.1 | 0.1 |
| 330 | 5.4 | 0.1 | 3.3 | 0.0 | 88.3 | 0.0 | 0.6 | 2.2 | 0.0 |
| 337 | 5.4 | 0.1 | 3.2 | 0.0 | 88.9 | 0.0 | 0.6 | 1.8 | 0.0 |
| 354 | 5.3 | 0.1 | 3.2 | 0.0 | 89.3 | 0.0 | 0.6 | 1.5 | 0.0 |
| 361 | 5.3 | 0.1 | 3.2 | 0.0 | 89.3 | 0.0 | 0.6 | 1.4 | 0.0 |
| 378 | 5.3 | 0.1 | 3.2 | 0.0 | 89.3 | 0.0 | 0.6 | 1.5 | 0.0 |
| 385 | 5.3 | 0.1 | 3.3 | 0.0 | 89.2 | 0.0 | 0.6 | 1.4 | 0.0 |
| 402 | 5.3 | 0.1 | 3.4 | 0.0 | 89.1 | 0.0 | 0.6 | 1.5 | 0.0 |
| 409 | 5.3 | 0.1 | 3.5 | 0.0 | 89.1 | 0.0 | 0.6 | 1.4 | 0.0 |
| 426 | 5.3 | 0.1 | 3.6 | 0.0 | 88.9 | 0.0 | 0.6 | 1.4 | 0.0 |
| 433 | 5.3 | 0.1 | 3.5 | 0.0 | 88.9 | 0.0 | 0.6 | 1.5 | 0.0 |
| 498 | 5.4 | 0.1 | 3.9 | 0.0 | 88.5 | 0.0 | 0.6 | 1.6 | 0.0 |
| 505 | 5.4 | 0.1 | 3.8 | 0.0 | 88.6 | 0.0 | 0.6 | 1.5 | 0.0 |
| 522 | 5.4 | 0.1 | 3.9 | 0.0 | 88.3 | 0.0 | 0.6 | 1.6 | 0.1 |
| 529 | 5.6 | 0.1 | 3.9 | 0.0 | 88.2 | 0.0 | 0.6 | 1.6 | 0.0 |
| 546 | 5.4 | 0.1 | 4.0 | 0.0 | 88.2 | 0.0 | 0.6 | 1.6 | 0.0 |
| 553 | 5.4 | 0.1 | 4.0 | 0.0 | 88.2 | 0.0 | 0.6 | 1.6 | 0.0 |
| 570 | 5.4 | 0.1 | 4.1 | 0.0 | 88.0 | 0.0 | 0.6 | 1.8 | 0.0 |
| 577 | 5.5 | 0.1 | 4.1 | 0.0 | 87.8 | 0.0 | 0.6 | 1.8 | 0.0 |
| 594 | 5.4 | 0.1 | 4.2 | 0.0 | 87.9 | 0.0 | 0.6 | 1.8 | 0.0 |
| 601 | 5.4 | 0.1 | 4.2 | 0.0 | 87.8 | 0.0 | 0.6 | 1.8 | 0.0 |
| 666 | 5.4 | 0.1 | 4.4 | 0.0 | 87.6 | 0.0 | 0.6 | 1.9 | 0.0 |
| 673 | 5.4 | 0.1 | 4.4 | 0.0 | 87.3 | 0.0 | 0.6 | 2.2 | 0.0 |
| 690 | 5.3 | 0.0 | 4.5 | 0.0 | 87.6 | 0.0 | 0.6 | 1.9 | 0.0 |

TABLE 2-continued

Composition of the product mixture according to Example 1 (data in % by mass)

| t [h] | HC[a] | IR[b] | AL[c] | FOR[d] | OL[e] | Ethers[f] | Esters[g] | Acetals[h] | Remainder |
|---|---|---|---|---|---|---|---|---|---|
| 697 | 5.4 | 0.0 | 4.5 | 0.0 | 87.5 | 0.0 | 0.6 | 1.9 | 0.1 |
| 714 | 5.3 | 0.0 | 4.6 | 0.0 | 87.5 | 0.0 | 0.6 | 1.9 | 0.0 |

[a]HC: hydrocarbons;
[b]Intermediate run;
[c]$C_9$-aldehydes;
[d]$C_9$-formates;
[e]C9-alcohols;
[f]$C_9/C_9$-ethers;
[g]$C_9/C_9$-esters;
[h]$C_9$-$C_9$-acetals.

Figure 1:
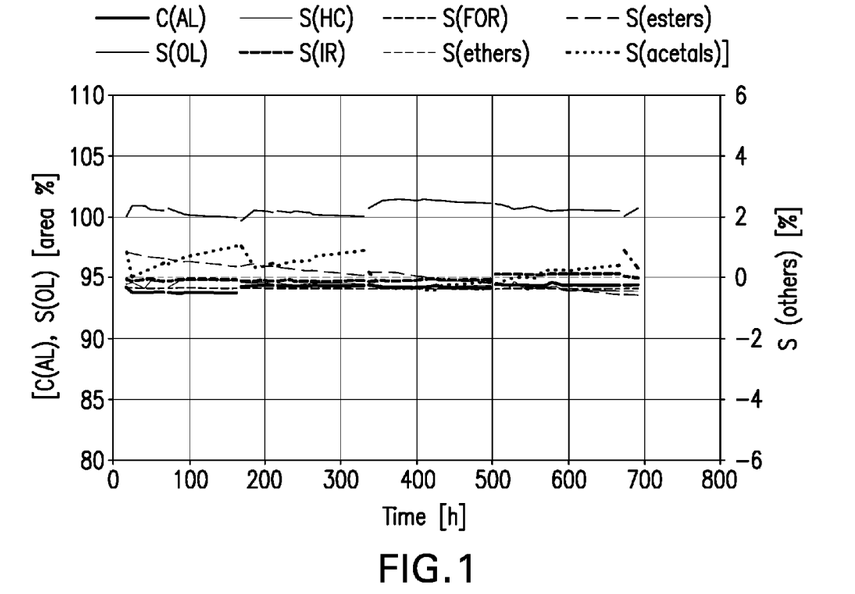
FIG. 1 shows a conversion selectivity diagram for the reaction described in Example 1.

An associated conversion selectivity diagram is shown in FIG. 1.

Example 2

The same use mixture and the same apparatus as in Example 1 were used. A chromium-free catalyst according to the invention was used. The composition of the resulting product mixture is shown in Table 3.

TABLE 3

Composition of the production mixture according to Example 2

| t [h] | HC[a] | IR[b] | AL[c] | FOR[d] | OL[e] | Ethers[f] | Esters[g] | Acetals[h] | remainder |
|---|---|---|---|---|---|---|---|---|---|
| 18 | 5.8 | 0.0 | 2.2 | 0.5 | 89.1 | 0.0 | 0.2 | 1.8 | 0.3 |
| 25 | 5.8 | 0.0 | 2.4 | 0.4 | 88.4 | 0.0 | 0.7 | 2.0 | 0.2 |
| 41 | 5.8 | 0.0 | 2.5 | 0.5 | 88.1 | 0.0 | 0.6 | 2.2 | 0.3 |
| 49 | 6.2 | 0.0 | 2.6 | 0.6 | 87.5 | 0.0 | 0.5 | 2.3 | 0.3 |
| 66 | 6.2 | 0.0 | 2.6 | 0.6 | 87.3 | 0.0 | 0.7 | 2.3 | 0.3 |
| 73 | 6.5 | 0.0 | 2.9 | 0.7 | 85.9 | 0.0 | 0.9 | 2.8 | 0.2 |
| 90 | 6.5 | 0.0 | 2.8 | 0.6 | 86.6 | 0.0 | 0.5 | 2.8 | 0.1 |
| 97 | 6.5 | 0.0 | 3.0 | 0.7 | 86.0 | 0.0 | 0.8 | 2.9 | 0.2 |
| 162 | 6.3 | 0.0 | 3.5 | 0.7 | 85.3 | 0.0 | 0.6 | 3.5 | 0.1 |
| 169 | 6.5 | 0.0 | 3.3 | 0.7 | 85.6 | 0.0 | 0.6 | 3.2 | 0.1 |
| 186 | 6.6 | 0.0 | 3.3 | 0.7 | 85.7 | 0.0 | 0.5 | 3.2 | 0.1 |
| 193 | 6.5 | 0.0 | 3.3 | 0.7 | 85.7 | 0.0 | 0.5 | 3.3 | 0.0 |
| 210 | 6.6 | 0.0 | 3.4 | 0.7 | 85.7 | 0.0 | 0.5 | 3.0 | 0.0 |
| 217 | 6.3 | 0.0 | 3.5 | 0.7 | 85.4 | 0.0 | 0.5 | 3.6 | 0.0 |
| 234 | 5.8 | 0.0 | 3.4 | 0.5 | 87.3 | 0.0 | 0.4 | 2.6 | 0.0 |
| 241 | 5.8 | 0.0 | 3.4 | 0.5 | 87.1 | 0.0 | 0.6 | 2.3 | 0.2 |
| 260 | 5.7 | 0.0 | 3.4 | 0.4 | 87.3 | 0.0 | 0.6 | 2.3 | 0.2 |
| 330 | 5.8 | 0.0 | 4.2 | 0.5 | 85.9 | 0.0 | 0.6 | 2.3 | 0.7 |
| 337 | 5.8 | 0.0 | 4.1 | 0.4 | 86.4 | 0.0 | 0.6 | 2.6 | 0.0 |
| 354 | 5.9 | 0.0 | 4.2 | 0.4 | 86.4 | 0.0 | 0.5 | 2.5 | 0.0 |
| 361 | 5.8 | 0.0 | 4.4 | 0.5 | 86.0 | 0.0 | 0.7 | 2.5 | 0.2 |
| 378 | 5.9 | 0.0 | 4.4 | 0.3 | 86.3 | 0.0 | 0.5 | 2.6 | 0.0 |
| 385 | 6.0 | 0.0 | 4.4 | 0.3 | 86.2 | 0.0 | 0.5 | 2.6 | 0.0 |
| 402 | 6.0 | 0.0 | 4.5 | 0.3 | 85.7 | 0.0 | 0.5 | 2.8 | 0.0 |
| 409 | 6.0 | 0.0 | 4.7 | 0.4 | 86.5 | 0.0 | 0.2 | 2.1 | 0.0 |
| 426 | 5.9 | 0.0 | 4.7 | 0.4 | 86.1 | 0.0 | 0.6 | 2.5 | 0.0 |
| 433 | 5.9 | 0.0 | 5.0 | 0.4 | 86.5 | 0.0 | 0.0 | 2.2 | 0.0 |
| 498 | 5.9 | 0.0 | 5.1 | 0.3 | 85.6 | 0.0 | 0.5 | 2.6 | 0.0 |
| 505 | 5.9 | 0.0 | 5.3 | 0.3 | 85.3 | 0.0 | 0.6 | 2.7 | 0.0 |
| 522 | 5.8 | 0.0 | 5.6 | 0.5 | 84.8 | 0.0 | 0.6 | 2.6 | 0.0 |
| 529 | 5.9 | 0.0 | 5.3 | 0.4 | 85.2 | 0.0 | 0.6 | 2.7 | 0.0 |
| 546 | 5.7 | 0.0 | 5.6 | 0.6 | 84.8 | 0.0 | 0.6 | 2.6 | 0.0 |
| 553 | 5.7 | 0.0 | 5.8 | 0.6 | 84.5 | 0.0 | 0.5 | 2.8 | 0.0 |
| 570 | 5.5 | 0.0 | 5.4 | 0.3 | 85.8 | 0.0 | 0.4 | 2.5 | 0.0 |
| 577 | 5.7 | 0.0 | 5.6 | 0.3 | 85.6 | 0.0 | 0.3 | 2.4 | 0.0 |
| 593 | 5.7 | 0.0 | 5.9 | 0.4 | 85.1 | 0.0 | 0.4 | 2.4 | 0.0 |
| 601 | 5.7 | 0.0 | 5.7 | 0.3 | 85.4 | 0.0 | 0.4 | 2.5 | 0.1 |
| 673 | 5.6 | 0.0 | 5.9 | 0.3 | 85.5 | 0.0 | 0.6 | 2.1 | 0.1 |
| 690 | 5.7 | 0.0 | 6.0 | 0.3 | 84.6 | 0.0 | 0.6 | 2.8 | 0.0 |
| 714 | 5.7 | 0.0 | 4.5 | 0.3 | 86.3 | 0.0 | 0.6 | 2.4 | 0.1 |
| 721 | 5.6 | 0.0 | 4.4 | 0.2 | 86.4 | 0.0 | 0.6 | 2.7 | 0.0 |
| 738 | 5.5 | 0.0 | 4.4 | 0.2 | 86.5 | 0.0 | 0.7 | 2.7 | 0.0 |
| 837 | 5.7 | 0.0 | 4.9 | 0.2 | 86.1 | 0.0 | 0.3 | 2.4 | 0.4 |
| 845 | 5.7 | 0.0 | 5.0 | 0.3 | 85.9 | 0.0 | 0.4 | 2.4 | 0.4 |
| 862 | 5.5 | 0.0 | 5.0 | 0.2 | 86.1 | 0.0 | 0.3 | 2.4 | 0.4 |
| 869 | 5.5 | 0.0 | 5.2 | 0.3 | 85.8 | 0.0 | 0.0 | 2.8 | 0.3 |

TABLE 3-continued

Composition of the production mixture according to Example 2

| t [h] | HC[a] | IR[b] | AL[c] | FOR[d] | OL[e] | Ethers[f] | Esters[g] | Acetals[h] | remainder |
|---|---|---|---|---|---|---|---|---|---|
| 886 | 5.6 | 0.0 | 5.2 | 0.3 | 86.1 | 0.0 | 0.1 | 2.3 | 0.4 |
| 893 | 5.6 | 0.0 | 5.4 | 0.2 | 85.9 | 0.0 | 0.2 | 2.4 | 0.4 |
| 908 | 5.6 | 0.0 | 5.4 | 0.2 | 85.9 | 0.0 | 0.2 | 2.4 | 0.4 |
| 916 | 5.6 | 0.0 | 5.6 | 0.3 | 84.9 | 0.0 | 0.4 | 2.7 | 0.3 |
| 933 | 5.7 | 0.0 | 5.6 | 0.3 | 85.0 | 0.0 | 0.4 | 2.7 | 0.3 |
| 941 | 5.4 | 0.0 | 5.6 | 0.2 | 85.8 | 0.0 | 0.2 | 2.4 | 0.3 |
| 1006 | 5.6 | 0.0 | 6.3 | 0.0 | 85.1 | 0.0 | 0.3 | 2.3 | 0.3 |
| 1013 | 5.7 | 0.0 | 6.3 | 0.0 | 85.2 | 0.0 | 0.3 | 2.2 | 0.3 |
| 1030 | 5.4 | 0.0 | 6.1 | 0.0 | 86.6 | 0.0 | 0.0 | 1.8 | 0.0 |
| 1037 | 5.7 | 0.0 | 8.9 | 0.0 | 81.8 | 0.0 | 0.5 | 3.1 | 0.0 |
| 1054 | 5.8 | 0.0 | 9.0 | 0.0 | 81.6 | 0.0 | 0.5 | 3.1 | 0.0 |
| 1063 | 5.5 | 0.0 | 5.8 | 0.0 | 85.0 | 0.0 | 0.5 | 3.2 | 0.0 |
| 1077 | 5.5 | 0.0 | 5.8 | 0.0 | 85.0 | 0.0 | 0.5 | 3.1 | 0.0 |
| 1085 | 5.6 | 0.0 | 5.9 | 0.0 | 84.9 | 0.0 | 0.5 | 3.1 | 0.0 |
| 1100 | 5.6 | 0.0 | 6.0 | 0.0 | 84.2 | 0.0 | 0.5 | 3.6 | 0.0 |
| 1109 | 5.7 | 0.0 | 6.1 | 0.0 | 84.0 | 0.0 | 0.4 | 3.7 | 0.1 |
| 1170 | 5.7 | 0.0 | 6.2 | 0.0 | 84.0 | 0.0 | 0.4 | 3.7 | 0.1 |

Figure 2:
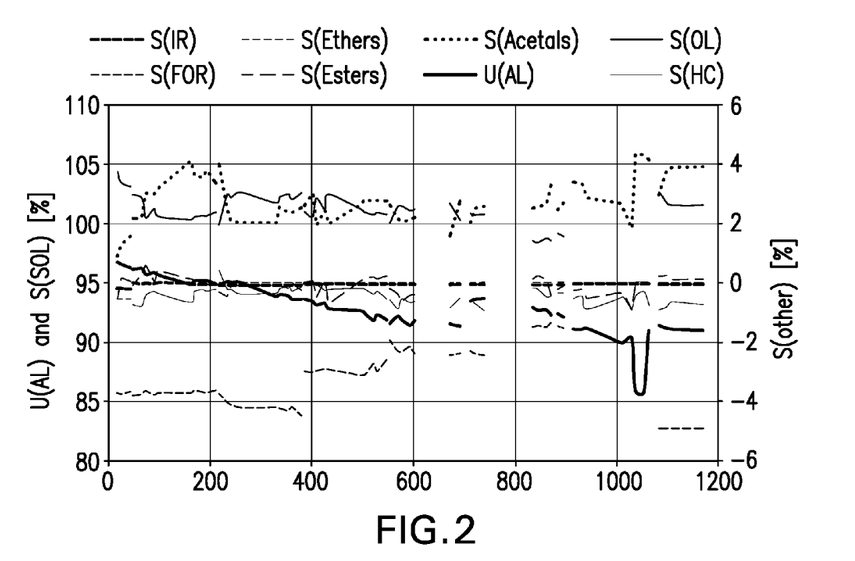
FIG. 2 shows a conversion-selectivity diagram for the reaction of Example 2.

FIG. 2 shows a corresponding conversion-selectivity diagram

Example 3

A reaction discharge from the rhodium-catalysed hydroformylation of dibutene was continuously hydrogenated in a circulation apparatus at 180° C. and 25 bar absolute over 150 g of catalyst in the liquid phase. Per hour, 0.1 l of starting material were pushed through for a circulation of 20 l/h. The amount of off-gas was 0.5 l/h (STP). A chromium-free Ni/Cu catalyst on $Al_2O_3$ support material produced according to Example 0 was used. The composition of the use mixture used is shown in Table 4.

TABLE 4

Composition of the use mixture comprising C9-aldehydes

| Component | HC[a] | IR[b] | AL[c] | FOR[d] | OL[e] | Ethers[f] | Esters[g] | Acetals[h] | Water | Remainder |
|---|---|---|---|---|---|---|---|---|---|---|
| content [% by mass] | 6.5 | 0.1 | 90.3 | 0.6 | 2.5 | 0.0 | 0.0 | 0.1 | 0.0 | 0.0 |

[a]HC: hydrocarbons;
[b]Intermediate run;
[c]$C_9$-aldehydes;
[d]$C_9$-formates;
[e]C9-alcohols;
[f]$C_9/C_9$-ethers;
[g]$C_9/C_9$-esters;
[h]$C_9/C_9$-acetals, The course over time of the composition of the product mixture is shown in Table 5:

TABLE 5

Course over time of the composition of the product mixture

| t [h] | HC[a] | IR[b] | AL[c] | FOR[d] | OL[e] | Ethers[f] | Esters[g] | Acetals[h] | Water | Remainder |
|---|---|---|---|---|---|---|---|---|---|---|
| 0 | 6.4 | 0.1 | 59.1 | 0.0 | 32.9 | 0.5 | 0.7 | 0.2 | 0.0 | 0.1 |
| 1 | 6.3 | 0.1 | 0.9 | 0.0 | 91.8 | 0.3 | 0.4 | 0.2 | 0.0 | 0.1 |
| 2 | 6.4 | 0.1 | 0.0 | 0.0 | 92.4 | 0.3 | 0.4 | 0.2 | 0.0 | 0.1 |
| 3 | 6.4 | 0.1 | 0.1 | 0.0 | 92.4 | 0.4 | 0.4 | 0.1 | 0.0 | 0.1 |
| 5 | 6.3 | 0.1 | 0.1 | 0.0 | 92.3 | 0.4 | 0.7 | 0.0 | 0.0 | 0.1 |
| 22 | 6.4 | 0.1 | 0.0 | 0.0 | 92.4 | 0.5 | 0.5 | 0.0 | 0.0 | 0.1 |
| 46 | 6.4 | 0.0 | 0.0 | 0.0 | 92.5 | 0.6 | 0.4 | 0.0 | 0.0 | 0.0 |
| 70 | 6.4 | 0.0 | 0.0 | 0.0 | 91.9 | 1.3 | 0.4 | 0.0 | 0.0 | 0.0 |
| 142 | 6.4 | 0.2 | 0.0 | 0.1 | 91.0 | 1.9 | 0.3 | 0.0 | 0.0 | 0.0 |
| 166 | 6.4 | 0.0 | 0.0 | 0.0 | 91.3 | 2.0 | 0.3 | 0.0 | 0.0 | 0.0 |
| 190 | 6.4 | 0.3 | 0.0 | 0.1 | 90.4 | 2.4 | 0.3 | 0.0 | 0.0 | 0.0 |
| 214 | 6.4 | 0.0 | 0.0 | 0.0 | 91.0 | 2.2 | 0.3 | 0.0 | 0.0 | 0.0 |
| 238 | 6.4 | 0.0 | 0.0 | 0.0 | 90.9 | 2.3 | 0.3 | 0.0 | 0.0 | 0.0 |
| 310 | 6.3 | 0.1 | 0.0 | 0.0 | 90.7 | 2.6 | 0.3 | 0.0 | 0.0 | 0.0 |
| 335 | 6.2 | 0.1 | 0.0 | 0.0 | 90.8 | 2.7 | 0.2 | 0.0 | 0.0 | 0.0 |
| 358 | 6.2 | 0.1 | 0.0 | 0.0 | 90.7 | 2.8 | 0.2 | 0.0 | 0.0 | 0.0 |
| 382 | 6.2 | 0.0 | 0.0 | 0.0 | 90.7 | 2.8 | 0.2 | 0.0 | 0.0 | 0.0 |
| 406 | 6.2 | 0.1 | 0.0 | 0.0 | 90.6 | 2.9 | 0.2 | 0.0 | 0.0 | 0.0 |

TABLE 5-continued

Course over time of the composition of the product mixture

| t [h] | HC[a] | IR[b] | AL[c] | FOR[d] | OL[e] | Ethers[f] | Esters[g] | Acetals[h] | Water | Remainder |
|---|---|---|---|---|---|---|---|---|---|---|
| 478 | 6.1 | 0.1 | 0.0 | 0.0 | 90.5 | 3.0 | 0.2 | 0.0 | 0.0 | 0.0 |
| 502 | 6.2 | 0.1 | 0.0 | 0.0 | 90.5 | 3.0 | 0.2 | 0.0 | 0.0 | 0.0 |
| 526 | 6.2 | 0.1 | 0.0 | 0.0 | 90.6 | 3.0 | 0.2 | 0.0 | 0.0 | 0.0 |
| 550 | 6.2 | 0.1 | 0.0 | 0.0 | 90.5 | 3.0 | 0.2 | 0.0 | 0.0 | 0.0 |
| 575 | 6.1 | 0.1 | 0.0 | 0.0 | 90.6 | 3.0 | 0.2 | 0.0 | 0.0 | 0.0 |
| 646 | 6.2 | 0.1 | 0.0 | 0.0 | 90.5 | 3.0 | 0.2 | 0.0 | 0.0 | 0.0 |
| 670 | 6.2 | 0.1 | 0.0 | 0.0 | 90.8 | 2.8 | 0.1 | 0.0 | 0.0 | 0.0 |
| 694 | 6.2 | 0.1 | 0.0 | 0.0 | 90.5 | 3.0 | 0.2 | 0.0 | 0.0 | 0.0 |
| 718 | 6.2 | 0.1 | 0.0 | 0.0 | 90.5 | 3.0 | 0.2 | 0.0 | 0.0 | 0.0 |
| 743 | 6.2 | 0.1 | 0.0 | 0.0 | 90.6 | 3.0 | 0.2 | 0.0 | 0.0 | 0.0 |
| 814 | 6.2 | 0.1 | 0.0 | 0.0 | 90.6 | 2.9 | 0.2 | 0.0 | 0.0 | 0.0 |
| 838 | 6.2 | 0.1 | 0.0 | 0.0 | 90.6 | 2.9 | 0.2 | 0.0 | 0.0 | 0.0 |
| 863 | 6.2 | 0.1 | 0.0 | 0.0 | 90.7 | 2.9 | 0.2 | 0.0 | 0.0 | 0.0 |
| 982 | 6.3 | 0.1 | 0.0 | 0.0 | 90.7 | 2.8 | 0.1 | 0.0 | 0.0 | 0.0 |
| 1009 | 6.4 | 0.1 | 0.0 | 0.0 | 92.3 | 1.3 | 0.0 | 0.0 | 0.0 | 0.0 |
| 1054 | 6.2 | 0.1 | 0.0 | 0.0 | 90.9 | 2.7 | 0.1 | 0.0 | 0.0 | 0.0 |

Example 4

Pure 1-nonanal was hydrogenated continuously in a trickle-bed apparatus at a temperature of 180° C. and a pressure of $25*10^5$ Pa absolute over 3 g of catalyst in the liquid phase. Per hour, 0.12 l of starting material were pushed through. The amount of off-gas was 20 l/h (STP). A chromium-free Ni/Cu catalyst on $Al_2O_3$ support material prepared according to Example 0 was used. However, the catalyst was used as powder in order to counteract mass transfer problems. Scalability to industrial pellets, however, was further given. The course over time of the composition of the product mixture is shown in Table 6:

TABLE 6

Course over time of the composition of the product mixture according to Example 4

| t [h] | HC | AL | FOR | OL | Ethers | Acid | Mono-hydrogenated enal | Esters | Enal | Hydrogenated enal | Acetals | HB |
|---|---|---|---|---|---|---|---|---|---|---|---|---|
| 18 | 0.21 | 0.09 | 0.05 | 85.73 | 0.49 | 0.12 | 0.01 | 2.29 | 0.27 | 4.86 | 0.06 | 5.08 |
| 42 | 0.18 | 0.05 | 0.04 | 86.75 | 0.27 | 0.10 | 0.01 | 2.42 | 0.19 | 4.59 | 0.07 | 4.60 |
| 66 | 0.16 | 0.04 | 0.04 | 85.39 | 0.36 | 0.11 | 0.00 | 2.83 | 0.18 | 5.19 | 0.09 | 4.68 |
| 144 | 0.26 | 0.03 | 0.04 | 83.86 | 0.89 | 0.08 | 0.00 | 3.13 | 0.36 | 4.97 | 0.16 | 4.97 |
| 162 | 0.24 | 0.10 | 0.04 | 84.55 | 0.85 | 0.05 | 0.00 | 3.05 | 0.30 | 4.69 | 0.15 | 4.91 |
| 186 | 0.20 | 0.05 | 0.04 | 83.42 | 0.78 | 0.03 | 0.00 | 3.56 | 0.27 | 5.23 | 0.13 | 4.98 |
| 210 | 0.20 | 0.05 | 0.04 | 82.93 | 0.78 | 0.03 | 0.00 | 3.88 | 0.29 | 5.49 | 0.15 | 4.70 |
| 234 | 0.19 | 0.04 | 0.04 | 82.52 | 0.85 | 0.03 | 0.00 | 3.94 | 0.27 | 5.44 | 0.17 | 5.14 |
| 306 | 0.19 | 0.04 | 0.04 | 82.85 | 0.78 | 0.02 | 0.00 | 3.93 | 0.24 | 5.32 | 0.17 | 5.07 |
| 330 | 0.18 | 0.04 | 0.00 | 83.41 | 0.80 | 0.03 | 0.00 | 4.02 | 0.23 | 5.40 | 0.18 | 4.29 |
| 354 | 0.17 | 0.04 | 0.00 | 82.53 | 0.81 | 0.02 | 0.00 | 4.16 | 0.21 | 5.56 | 0.18 | 4.96 | t: time,

HC: other hydrocarbons,

AL: aldehydes,

FOR: formates,

OL: alcohol,

HB: high boilers

Example 5

Not According to the Invention

The experiment described in Example 4 was carried out analogously with the same starting material and under the same conditions. However, a chromium-containing catalyst was used as was also used for the experiments described in DE19842370A1. The course over time of the composition of the product mixture is shown in Table 7:

TABLE 7

Course over time of the composition of the product mixture according to Example 5

| t [h] | HC | AL | FOR | OL | Ethers | Acid | Mono-hydrogenated enal | Esters | Enal | Hydrogenated enal | Acetals | HB |
|---|---|---|---|---|---|---|---|---|---|---|---|---|
| 18.0 | 0.16 | 0.39 | 0.04 | 83.39 | 0.41 | 0.03 | 0.00 | 2.49 | 0.36 | 4.89 | 0.08 | 6.86 |
| 42.0 | 0.16 | 0.07 | 0.03 | 84.82 | 0.39 | 0.02 | 0.01 | 2.41 | 0.23 | 4.09 | 0.26 | 6.71 |
| 66.0 | 0.15 | 0.05 | 0.03 | 84.77 | 0.45 | 0.02 | 0.01 | 2.52 | 0.20 | 4.53 | 0.14 | 6.16 |
| 138.0 | 0.29 | 0.71 | 0.04 | 83.45 | 0.70 | 0.16 | 0.00 | 2.62 | 0.51 | 4.05 | 0.19 | 6.22 |
| 144.0 | 0.20 | 0.02 | 0.03 | 84.28 | 0.77 | 0.05 | 0.00 | 2.64 | 0.28 | 4.10 | 0.11 | 6.57 |
| 162.0 | 0.21 | 0.05 | 0.03 | 84.85 | 0.72 | 0.02 | 0.00 | 2.60 | 0.27 | 4.07 | 0.12 | 6.07 |
| 186.0 | 0.18 | 0.05 | 0.03 | 83.48 | 0.69 | 0.03 | 0.00 | 3.09 | 0.25 | 4.67 | 0.16 | 5.98 |
| 210.0 | 0.17 | 0.04 | 0.03 | 83.14 | 0.69 | 0.02 | 0.00 | 3.37 | 0.23 | 4.79 | 0.17 | 5.88 |
| 234.0 | 0.17 | 0.04 | 0.04 | 84.37 | 0.68 | 0.02 | 0.00 | 3.17 | 0.21 | 4.37 | 0.15 | 5.43 |
| 306.0 | 0.19 | 0.04 | 0.00 | 83.27 | 0.71 | 0.02 | 0.00 | 3.54 | 0.07 | 4.71 | 0.18 | 5.76 |
| 330.0 | 0.18 | 0.03 | 0.00 | 82.68 | 0.73 | 0.02 | 0.00 | 3.81 | 0.08 | 5.06 | 0.19 | 5.69 |
| 354.0 | 0.18 | 0.04 | 0.00 | 83.00 | 0.72 | 0.02 | 0.00 | 3.67 | 0.07 | 4.91 | 0.19 | 5.64 | t: time,
HC: other hydrocarbons,
AL: aldehydes,
FOR: formates,
OL: alcohol,
HB: high boilers

Example 6

A reaction discharge from the cobalt-catalysed hydroformylation of butene was continuously hydrogenated in a trickle-bed apparatus at 120° C. and 25 bar absolute over 3 g of catalyst in the liquid phase. Per hour, 0.12 l of starting material were used. The amount of off-gas was 20 l/h (STP). A chromium-free Ni/Cu catalyst on $Al_2O_3$ support material produced according to Example 0 was used. However, the catalyst was used as powder in order to counteract mass transfer problems. Scalability to technical pellets, however, was further given. The course over time of the composition of the product mixture is shown in Table 8; the composition of the starting material mixture corresponds here to the table entry at time t=0.

Example 7

Not According to the Invention

The experiment described in Example 6 was carried out analogously with the same starting material and under the same conditions. However, a chromium-containing catalyst was used as was also used for the experiments described in DE19842370A1. The course over time of the composition of the product mixture is shown in Table 9; the composition of the starting material mixture corresponds here to the table entry at time t=0.

TABLE 8

Course over time of the composition of the product mixture according to Example 6

| t [h] | Alkanes | 2-Methyl-1-butanal | n-Pentanal | 2-Methyl-1-butanol | n-Pentanol | Pentanoic acid | 2-Propyl-2-heptenal | Unknown |
|---|---|---|---|---|---|---|---|---|
| 0 | 0.57 | 4.59 | 86.66 | 0.00 | 0.12 | 0.12 | 1.29 | 4.57 |
| 16.4 | 0.08 | 0.10 | 0.29 | 4.32 | 75.71 | 0.15 | 5.40 | 11.60 |
| 88.7 | 0.09 | 0.01 | 0.01 | 4.71 | 83.60 | 0.00 | 0.41 | 10.08 |
| 114.1 | 0.09 | 0.05 | 0.15 | 4.61 | 82.57 | 0.15 | 0.74 | 10.24 |
| 138.3 | 0.09 | 0.14 | 1.74 | 4.18 | 76.17 | 0.20 | 0.77 | 13.29 |
| 184.8 | 0.09 | 0.33 | 2.57 | 4.03 | 75.13 | 0.22 | 0.70 | 14.74 |
| 256.6 | 0.09 | 0.14 | 0.59 | 4.51 | 82.42 | 0.24 | 0.15 | 10.10 |
| 286.7 | 0.09 | 0.16 | 0.76 | 4.41 | 82.12 | 0.26 | 0.07 | 10.90 |

TABLE 9

Course over time of the composition of the product mixture according to Example 7

| t [h] | Alkanes | 2-Methyl-1-butanal | n-Pentanal | 2-Methyl-1-butanol | n-Pentanol | Pentanoic acid | 2-Propyl-2-heptenal | Unknown |
|---|---|---|---|---|---|---|---|---|
| 0 | 0.57 | 4.59 | 86.66 | 0.00 | 0.12 | 0.12 | 1.29 | 4.57 |
| 16.4 | 0.02 | 0.06 | 0.39 | 1.09 | 19.23 | 0.00 | 1.02 | 3.14 |
| 88.7 | 0.11 | 0.18 | 0.90 | 4.46 | 79.31 | 0.19 | 0.56 | 12.34 |
| 114.1 | 0.11 | 0.12 | 0.26 | 4.52 | 79.57 | 0.21 | 0.63 | 12.73 |
| 138.3 | 0.12 | 0.30 | 1.33 | 4.26 | 78.78 | 0.21 | 0.57 | 11.57 |
| 184.8 | 0.11 | 0.56 | 2.45 | 3.94 | 77.56 | 0.27 | 0.64 | 11.68 |
| 256.6 | 0.13 | 1.09 | 4.18 | 3.48 | 77.77 | 0.26 | 1.18 | 7.28 |
| 286.7 | 0.13 | 1.28 | 5.80 | 3.31 | 76.24 | 0.27 | 1.06 | 9.45 |

Example 8

A mixture of valeraldehyde and 2-propylheptanol was subjected to a continuous hydrogenation over a catalyst produced according to Example 0. The amount of catalyst was 60.9 g. The temperature was 180° C., the pressure 25*10⁵ Pa. The starting material feed was 0.12 l/h. The circulation was adjusted to 45 l/h. The amount of off-gas withdrawn was 1 l/min (STP). The course over time of the composition of the product mixture is shown in Table 10; the composition of the starting material mixture corresponds here to the table entry at time t=0.

TABLE 10

Course over time of the composition of the product mixture according to Example 8

| t [h] | 2-Methyl-butanel | n-Pentanal | 2-Me-1-Butanol | n-Pentanol | 4-Me-2-Pr-2-Hexenal | 4-Me-2-Pr-2-Hexanal | 4-Me-2-Pr-2-Hexenol | 4-Me-2-Pr-2-Hexanol | 2-Pr-2-Heptenal (1) unbr. | 2-Pr-2-Heptenal (2) br. | 2-PH-ol | 2-PHE-ol | Unknown |
|---|---|---|---|---|---|---|---|---|---|---|---|---|---|
| 0 | 1.64 | 13.18 | 0.01 | 0.14 | 1.91 | 0.95 | 0.00 | 0.00 | 0.00 | 81.50 | 0.00 | 0.00 | 0.67 |
| 0 | 8.87 | 70.84 | 0.04 | 0.78 | 10.37 | 5.22 | 0.06 | 0.00 | 0.00 | 0.27 | 0.00 | 0.00 | 3.55 |
| 0 | 0.01 | 0.07 | 1.66 | 12.64 | 0.01 | 0.40 | 1.73 | 0.26 | 0.47 | 0.04 | 81.91 | 0.00 | 0.80 |
| 17 | 0.01 | 0.11 | 1.69 | 13.07 | 0.01 | 0.33 | 1.73 | 0.13 | 0.66 | 0.06 | 81.49 | 0.00 | 0.72 |
| 89 | 0.01 | 0.06 | 1.71 | 13.26 | 0.02 | 0.42 | 1.73 | 0.07 | 0.32 | 0.02 | 81.75 | 0.00 | 0.62 |
| 96 | 0.01 | 0.06 | 1.71 | 13.20 | 0.02 | 0.44 | 1.73 | 0.07 | 0.33 | 0.03 | 81.77 | 0.00 | 0.62 |
| 113 | 0.01 | 0.06 | 1.71 | 13.19 | 0.02 | 0.43 | 1.73 | 0.07 | 0.32 | 0.02 | 81.81 | 0.00 | 0.62 |
| 120 | 0.01 | 0.06 | 1.71 | 13.19 | 0.02 | 0.43 | 1.73 | 0.07 | 0.32 | 0.02 | 81.80 | 0.00 | 0.62 |
| 137 | 0.01 | 0.06 | 1.72 | 13.22 | 0.02 | 0.44 | 1.73 | 0.08 | 0.32 | 0.02 | 81.75 | 0.00 | 0.63 |
| 144 | 0.01 | 0.06 | 1.72 | 13.21 | 0.02 | 0.44 | 1.73 | 0.07 | 0.32 | 0.02 | 81.76 | 0.00 | 0.63 |
| 161 | 0.01 | 0.06 | 1.71 | 13.20 | 0.02 | 0.45 | 1.73 | 0.07 | 0.32 | 0.03 | 81.77 | 0.00 | 0.63 |
| 167 | 0.01 | 0.06 | 1.72 | 13.29 | 0.02 | 0.46 | 1.73 | 0.07 | 0.31 | 0.02 | 81.67 | 0.00 | 0.63 |
| 188 | 0.01 | 0.06 | 1.72 | 13.28 | 0.03 | 0.45 | 1.73 | 0.07 | 0.32 | 0.02 | 81.68 | 0.00 | 0.62 |
| 192 | 0.01 | 0.06 | 1.71 | 13.25 | 0.03 | 0.46 | 1.73 | 0.07 | 0.33 | 0.03 | 81.70 | 0.00 | 0.62 |
| 257 | 0.01 | 0.07 | 1.71 | 13.27 | 0.03 | 0.48 | 1.73 | 0.07 | 0.34 | 0.03 | 81.66 | 0.00 | 0.61 |
| 281 | 0.01 | 0.05 | 1.69 | 10.87 | 0.03 | 0.50 | 1.78 | 0.06 | 0.36 | 0.03 | 84.01 | 0.00 | 0.61 |
| 288 | 0.01 | 0.05 | 1.69 | 10.59 | 0.03 | 0.39 | 1.79 | 0.06 | 0.35 | 0.03 | 84.42 | 0.00 | 0.61 |
| 306 | 0.01 | 0.05 | 1.62 | 13.38 | 0.03 | 0.48 | 0.07 | 1.73 | 0.06 | 0.35 | 81.65 | 0.00 | 0.59 |
| 312 | 0.01 | 0.05 | 1.68 | 10.34 | 0.03 | 0.51 | 1.79 | 0.06 | 0.36 | 0.03 | 84.54 | 0.00 | 0.61 |
| 329 | 0.01 | 0.05 | 1.68 | 10.36 | 0.01 | 0.51 | 1.79 | 0.05 | 0.37 | 0.03 | 84.54 | 0.00 | 0.59 |
| 335 | 0.01 | 0.06 | 1.68 | 10.40 | 0.01 | 0.51 | 1.79 | 0.05 | 0.37 | 0.03 | 84.50 | 0.00 | 0.59 |
| 359 | 0.01 | 0.07 | 1.71 | 13.33 | 0.01 | 0.49 | 1.73 | 0.06 | 0.35 | 0.03 | 81.61 | 0.00 | 0.60 |
| 425 | 0.01 | 0.08 | 1.73 | 14.45 | 0.01 | 0.50 | 1.70 | 0.06 | 0.37 | 0.03 | 80.49 | 0.00 | 0.57 |
| 432 | 0.01 | 0.07 | 1.73 | 14.42 | 0.01 | 0.51 | 1.71 | 0.06 | 0.37 | 0.03 | 80.50 | 0.00 | 0.57 |
| 473 | 0.01 | 0.07 | 1.72 | 13.25 | 0.01 | 0.53 | 1.73 | 0.06 | 0.38 | 0.03 | 81.62 | 0.00 | 0.59 |
| 480 | 0.01 | 0.07 | 1.72 | 13.25 | 0.01 | 0.52 | 1.73 | 0.06 | 0.38 | 0.03 | 81.64 | 0.00 | 0.58 |
| 497 | 0.01 | 0.07 | 1.72 | 13.25 | 0.01 | 0.53 | 1.73 | 0.06 | 0.38 | 0.03 | 81.65 | 0.00 | 0.57 |
| 504 | 0.01 | 0.07 | 1.72 | 13.34 | 0.01 | 0.52 | 1.73 | 0.06 | 0.37 | 0.03 | 81.57 | 0.00 | 0.57 |
| 593 | 0.01 | 0.08 | 1.71 | 13.46 | 0.01 | 0.54 | 1.72 | 0.06 | 0.40 | 0.03 | 81.41 | 0.00 | 0.57 |
| 601 | 0.01 | 0.08 | 1.71 | 13.46 | 0.01 | 0.54 | 1.72 | 0.06 | 0.40 | 0.03 | 81.42 | 0.00 | 0.56 |
| 617 | 0.01 | 0.08 | 1.71 | 13.46 | 0.01 | 0.55 | 0.06 | 1.73 | 0.39 | 0.03 | 81.55 | 0.00 | 0.42 |
| 637 | 0.02 | 0.05 | 3.11 | 9.38 | 0.04 | 0.53 | 3.48 | 0.05 | 0.40 | 0.03 | 82.34 | 0.00 | 0.58 |
| 644 | 0.02 | 0.05 | 3.25 | 9.00 | 0.04 | 0.53 | 3.65 | 0.05 | 0.40 | 0.03 | 82.40 | 0.00 | 0.58 |
| 661 | 0.02 | 0.05 | 3.35 | 8.68 | 0.04 | 0.54 | 3.79 | 0.04 | 0.40 | 0.03 | 82.46 | 0.00 | 0.59 |
| 684 | 0.02 | 0.08 | 3.20 | 12.43 | 0.03 | 0.55 | 3.47 | 0.05 | 0.40 | 0.03 | 79.18 | 0.00 | 0.57 |
| 692 | 0.02 | 0.08 | 3.18 | 12.93 | 0.03 | 0.53 | 3.43 | 0.06 | 0.40 | 0.03 | 78.74 | 0.00 | 0.58 |
| 780 | 0.02 | 0.03 | 3.36 | 6.86 | 0.04 | 0.57 | 3.87 | 0.05 | 0.44 | 0.03 | 84.12 | 0.00 | 0.60 |
| 787 | 0.02 | 0.03 | 3.39 | 6.03 | 0.04 | 0.58 | 3.94 | 0.04 | 0.44 | 0.03 | 84.85 | 0.00 | 0.61 |
| 804 | 0.02 | 0.03 | 3.42 | 5.36 | 0.04 | 0.59 | 3.99 | 0.03 | 0.44 | 0.03 | 85.42 | 0.00 | 0.63 |
| 807 | 0.02 | 0.03 | 3.42 | 5.27 | 0.04 | 0.58 | 3.99 | 0.03 | 0.43 | 0.03 | 85.51 | 0.00 | 0.63 |
| 824 | 0.02 | 0.07 | 3.34 | 7.97 | 0.04 | 0.56 | 3.80 | 0.04 | 0.40 | 0.03 | 83.10 | 0.00 | 0.63 |
| 832 | 0.02 | 0.09 | 3.30 | 11.29 | 0.04 | 0.54 | 3.63 | 0.05 | 0.40 | 0.03 | 80.00 | 0.00 | 0.62 |
| 848 | 0.02 | 0.09 | 3.30 | 14.31 | 0.04 | 0.54 | 3.51 | 0.06 | 0.40 | 0.03 | 77.12 | 0.00 | 0.58 |
| 855 | 0.02 | 0.09 | 3.30 | 14.71 | 0.03 | 0.53 | 3.50 | 0.06 | 0.40 | 0.03 | 76.76 | 0.00 | 0.57 |
| 944 | 0.02 | 0.09 | 3.29 | 15.15 | 0.04 | 0.55 | 3.48 | 0.06 | 0.41 | 0.03 | 76.32 | 0.00 | 0.55 |
| 968 | 0.02 | 0.08 | 3.62 | 13.57 | 0.04 | 0.57 | 3.59 | 0.06 | 0.42 | 0.03 | 77.45 | 0.00 | 0.54 |
| 976 | 0.02 | 0.08 | 3.65 | 13.27 | 0.04 | 0.57 | 3.61 | 0.06 | 0.43 | 0.03 | 77.70 | 0.00 | 0.54 |

TABLE 10-continued

Course over time of the composition of the product mixture according to Example 8

| t [h] | 2-Methyl-butanel | n-Pentanal | 2-Me-1-Butanol | n-Pentanol | 4-Me-2-Pr-2-Hexenal | 4-Me-2-Pr-2-Hexanal | 4-Me-2-Pr-2-Hexenol | 4-Me-2-Pr-2-Hexanol | 2-Pr-2-Heptenal (1) unbr. | 2-Pr-2-Heptenal (2) br. | 2-PH-ol | 2-PHE-ol | Unknown |
|---|---|---|---|---|---|---|---|---|---|---|---|---|---|
| 992 | 0.02 | 0.08 | 3.70 | 13.19 | 0.04 | 0.58 | 3.62 | 0.06 | 0.43 | 0.03 | 77.72 | 0.00 | 0.54 |
| 1088 | 0.03 | 0.08 | 3.72 | 13.05 | 0.04 | 0.60 | 3.62 | 0.06 | 0.45 | 0.03 | 77.77 | 0.00 | 0.53 |
| 1096 | 0.03 | 0.08 | 3.73 | 13.05 | 0.04 | 0.61 | 3.63 | 0.06 | 0.44 | 0.03 | 77.77 | 0.00 | 0.53 |
| 1112 | 0.03 | 0.08 | 3.72 | 13.04 | 0.04 | 0.61 | 3.63 | 0.06 | 0.45 | 0.03 | 77.77 | 0.00 | 0.53 |
| 1120 | 0.03 | 0.08 | 3.74 | 13.00 | 0.04 | 0.61 | 3.63 | 0.06 | 0.46 | 0.04 | 77.80 | 0.00 | 0.53 |
| 1136 | 0.03 | 0.08 | 3.77 | 12.98 | 0.04 | 0.60 | 3.64 | 0.05 | 0.45 | 0.03 | 77.80 | 0.00 | 0.53 |
| 1143 | 0.03 | 0.09 | 3.77 | 12.99 | 0.04 | 0.61 | 3.64 | 0.05 | 0.47 | 0.04 | 77.75 | 0.00 | 0.52 |
| 1160 | 0.03 | 0.08 | 3.76 | 13.01 | 0.04 | 0.60 | 3.64 | 0.05 | 0.45 | 0.03 | 77.79 | 0.00 | 0.52 |
| 1184 | 0.03 | 0.09 | 3.77 | 12.99 | 0.04 | 0.61 | 3.64 | 0.05 | 0.46 | 0.03 | 77.77 | 0.00 | 0.53 |
| 1191 | 0.03 | 0.08 | 3.77 | 12.98 | 0.04 | 0.60 | 3.64 | 0.05 | 0.45 | 0.03 | 77.80 | 0.00 | 0.53 |
| 1256 | 0.03 | 0.09 | 3.77 | 12.97 | 0.04 | 0.61 | 3.63 | 0.05 | 0.47 | 0.03 | 77.79 | 0.00 | 0.53 |
| 1264 | 0.03 | 0.09 | 3.77 | 12.97 | 0.04 | 0.61 | 3.64 | 0.05 | 0.47 | 0.04 | 77.77 | 0.00 | 0.53 |
| 1280 | 0.03 | 0.09 | 3.76 | 12.98 | 0.04 | 0.62 | 3.64 | 0.05 | 0.47 | 0.04 | 77.77 | 0.00 | 0.53 |
| 1287 | 0.03 | 0.08 | 3.76 | 12.82 | 0.04 | 0.62 | 3.65 | 0.05 | 0.47 | 0.04 | 77.92 | 0.00 | 0.53 |
| 1304 | 0.03 | 0.08 | 3.75 | 12.64 | 0.04 | 0.61 | 3.65 | 0.05 | 0.46 | 0.04 | 78.13 | 0.00 | 0.52 |
| 1311 | 0.03 | 0.08 | 3.75 | 12.63 | 0.04 | 0.61 | 3.66 | 0.05 | 0.47 | 0.04 | 78.11 | 0.00 | 0.53 |
| 1328 | 0.03 | 0.09 | 3.75 | 12.62 | 0.05 | 0.62 | 3.65 | 0.05 | 0.48 | 0.04 | 78.07 | 0.00 | 0.56 |
| 1335 | 0.03 | 0.08 | 3.75 | 12.62 | 0.04 | 0.62 | 3.66 | 0.05 | 0.47 | 0.04 | 78.12 | 0.00 | 0.52 |
| 1352 | 0.03 | 0.09 | 3.75 | 12.63 | 0.04 | 0.62 | 3.66 | 0.05 | 0.49 | 0.04 | 78.08 | 0.00 | 0.53 |
| 1424 | 0.03 | 0.09 | 3.60 | 13.01 | 0.04 | 0.64 | 3.12 | 0.06 | 0.49 | 0.04 | 78.28 | 0.00 | 0.60 |
| 1432 | 0.03 | 0.09 | 3.60 | 13.01 | 0.04 | 0.64 | 3.12 | 0.06 | 0.49 | 0.04 | 78.30 | 0.00 | 0.59 |
| 1448 | 0.03 | 0.09 | 3.60 | 13.02 | 0.04 | 0.64 | 3.12 | 0.06 | 0.49 | 0.04 | 78.29 | 0.00 | 0.60 |
| 1455 | 0.03 | 0.09 | 3.59 | 12.99 | 0.04 | 0.64 | 3.12 | 0.06 | 0.48 | 0.04 | 78.34 | 0.00 | 0.60 |
| 1472 | 0.03 | 0.09 | 3.58 | 12.98 | 0.04 | 0.64 | 3.12 | 0.06 | 0.50 | 0.04 | 78.33 | 0.00 | 0.60 |
| 1502 | 0.03 | 0.09 | 3.58 | 13.02 | 0.04 | 0.63 | 3.05 | 0.09 | 0.49 | 0.04 | 78.22 | 0.00 | 0.72 |
| 1519 | 0.03 | 0.09 | 3.56 | 13.03 | 0.04 | 0.63 | 3.01 | 0.07 | 0.50 | 0.04 | 78.38 | 0.00 | 0.63 |
| 1590 | 0.03 | 0.09 | 3.54 | 13.13 | 0.03 | 0.65 | 2.95 | 0.07 | 0.52 | 0.05 | 78.33 | 0.00 | 0.62 |
| 1597 | 0.03 | 0.09 | 3.53 | 13.10 | 0.03 | 0.65 | 2.95 | 0.06 | 0.51 | 0.04 | 78.38 | 0.00 | 0.62 |
| 1614 | 0.03 | 0.09 | 3.54 | 13.14 | 0.04 | 0.65 | 2.95 | 0.06 | 0.51 | 0.04 | 78.32 | 0.00 | 0.62 |
| 1621 | 0.03 | 0.09 | 3.53 | 13.12 | 0.04 | 0.63 | 2.93 | 0.07 | 0.51 | 0.04 | 78.39 | 0.00 | 0.62 |
| 1638 | 0.03 | 0.09 | 3.53 | 13.20 | 0.04 | 0.65 | 2.91 | 0.07 | 0.51 | 0.04 | 78.31 | 0.00 | 0.63 |
| 1646 | 0.03 | 0.10 | 3.54 | 13.23 | 0.04 | 0.65 | 2.91 | 0.06 | 0.53 | 0.04 | 78.24 | 0.00 | 0.63 |
| 1662 | 0.03 | 0.10 | 3.53 | 13.22 | 0.04 | 0.67 | 2.90 | 0.06 | 0.53 | 0.04 | 78.12 | 0.00 | 0.78 |
| 1691 | 0.03 | 0.09 | 3.52 | 13.09 | 0.04 | 0.65 | 2.90 | 0.07 | 0.53 | 0.05 | 78.26 | 0.00 | 0.78 |
| 1698 | 0.03 | 0.09 | 3.52 | 13.11 | 0.03 | 0.66 | 2.90 | 0.06 | 0.51 | 0.04 | 78.42 | 0.00 | 0.62 |
| 1758 | 0.03 | 0.10 | 3.51 | 13.15 | 0.04 | 0.67 | 2.90 | 0.07 | 0.54 | 0.04 | 78.34 | 0.00 | 0.61 |
| 1781 | 0.03 | 0.10 | 3.53 | 13.15 | 0.04 | 0.68 | 2.90 | 0.06 | 0.55 | 0.04 | 78.31 | 0.00 | 0.61 |
| 1793 | 0.03 | 0.10 | 3.53 | 13.13 | 0.04 | 0.68 | 2.90 | 0.06 | 0.55 | 0.04 | 78.33 | 0.00 | 0.61 |
| 1806 | 0.03 | 0.10 | 3.52 | 13.11 | 0.04 | 0.68 | 2.90 | 0.07 | 0.56 | 0.05 | 78.34 | 0.00 | 0.61 |
| 1813 | 0.03 | 0.10 | 3.53 | 13.13 | 0.04 | 0.67 | 2.90 | 0.06 | 0.55 | 0.05 | 78.33 | 0.00 | 0.62 |
| 1829 | 0.03 | 0.10 | 3.52 | 13.08 | 0.04 | 0.67 | 2.90 | 0.07 | 0.55 | 0.05 | 78.39 | 0.00 | 0.62 |
| 1854 | 0.03 | 0.09 | 3.52 | 13.10 | 0.03 | 0.68 | 2.89 | 0.07 | 0.55 | 0.05 | 78.40 | 0.00 | 0.60 |
| 1865 | 0.03 | 0.10 | 3.52 | 13.09 | 0.03 | 0.67 | 2.89 | 0.07 | 0.56 | 0.04 | 78.38 | 0.00 | 0.61 |
| 1926 | 0.03 | 0.10 | 3.52 | 13.09 | 0.04 | 0.69 | 2.89 | 0.07 | 0.58 | 0.05 | 78.35 | 0.00 | 0.60 |
| 1954 | 0.03 | 0.10 | 3.52 | 13.08 | 0.04 | 0.69 | 2.90 | 0.06 | 0.57 | 0.05 | 78.37 | 0.00 | 0.61 |
| 1961 | 0.03 | 0.10 | 3.53 | 13.11 | 0.04 | 0.68 | 2.90 | 0.06 | 0.59 | 0.05 | 78.30 | 0.00 | 0.61 |
| 1974 | 0.03 | 0.10 | 3.50 | 13.03 | 0.04 | 0.69 | 2.89 | 0.07 | 0.58 | 0.05 | 78.41 | 0.00 | 0.61 |
| 1998 | 0.03 | 0.10 | 3.50 | 13.01 | 0.04 | 0.68 | 2.89 | 0.07 | 0.58 | 0.05 | 78.44 | 0.00 | 0.60 |
| 2022 | 0.03 | 0.10 | 3.50 | 13.03 | 0.04 | 0.69 | 2.89 | 0.07 | 0.58 | 0.05 | 78.41 | 0.00 | 0.61 |
| 2093 | 0.03 | 0.10 | 3.51 | 13.15 | 0.04 | 0.69 | 2.89 | 0.07 | 0.60 | 0.05 | 78.26 | 0.00 | 0.61 |
| 2117 | 0.03 | 0.10 | 3.51 | 13.19 | 0.04 | 0.71 | 2.89 | 0.07 | 0.59 | 0.05 | 78.22 | 0.00 | 0.60 |
| 2141 | 0.03 | 0.09 | 3.50 | 13.11 | 0.04 | 0.63 | 2.90 | 0.07 | 0.54 | 0.05 | 78.44 | 0.00 | 0.62 |
| 2165 | 0.03 | 0.09 | 3.50 | 13.08 | 0.03 | 0.64 | 2.90 | 0.08 | 0.54 | 0.04 | 78.45 | 0.00 | 0.62 |
| 2189 | 0.03 | 0.10 | 3.54 | 13.19 | 0.04 | 0.67 | 2.89 | 0.09 | 0.56 | 0.05 | 78.21 | 0.00 | 0.64 |
| 2261 | 0.03 | 0.11 | 3.37 | 13.08 | 0.04 | 0.78 | 2.86 | 0.08 | 0.64 | 0.05 | 78.33 | 0.00 | 0.63 |
| 2285 | 0.03 | 0.11 | 3.38 | 13.11 | 0.04 | 0.76 | 2.86 | 0.08 | 0.64 | 0.05 | 78.31 | 0.00 | 0.64 |
| 2309 | 0.03 | 0.11 | 3.33 | 13.11 | 0.04 | 0.74 | 2.85 | 0.08 | 0.63 | 0.05 | 78.39 | 0.00 | 0.64 |
| 2333 | 0.03 | 0.11 | 3.34 | 13.15 | 0.04 | 0.75 | 2.85 | 0.07 | 0.65 | 0.05 | 78.33 | 0.00 | 0.64 |
| 2358 | 0.03 | 0.11 | 3.33 | 13.13 | 0.04 | 0.76 | 2.85 | 0.07 | 0.64 | 0.05 | 78.35 | 0.00 | 0.64 |
| 2429 | 0.03 | 0.11 | 3.31 | 13.00 | 0.04 | 0.76 | 2.84 | 0.08 | 0.66 | 0.05 | 78.49 | 0.00 | 0.63 |
| 2453 | 0.03 | 0.11 | 3.31 | 13.03 | 0.04 | 0.77 | 2.85 | 0.07 | 0.65 | 0.05 | 78.45 | 0.00 | 0.64 |
| 2477 | 0.03 | 0.11 | 3.30 | 12.98 | 0.04 | 0.76 | 2.85 | 0.07 | 0.65 | 0.05 | 78.50 | 0.00 | 0.65 |
| 2501 | 0.03 | 0.11 | 3.30 | 12.97 | 0.04 | 0.76 | 2.85 | 0.07 | 0.66 | 0.05 | 78.52 | 0.00 | 0.64 |
| 2525 | 0.03 | 0.11 | 3.27 | 12.90 | 0.04 | 0.76 | 2.85 | 0.08 | 0.65 | 0.05 | 78.62 | 0.00 | 0.64 |
| 2597 | 0.03 | 0.11 | 3.29 | 13.04 | 0.05 | 0.79 | 2.84 | 0.07 | 0.68 | 0.05 | 78.41 | 0.00 | 0.64 |
| 2621 | 0.03 | 0.11 | 3.30 | 13.06 | 0.04 | 0.79 | 2.84 | 0.07 | 0.68 | 0.05 | 78.38 | 0.00 | 0.64 |
| 2645 | 0.03 | 0.11 | 3.29 | 13.07 | 0.05 | 0.79 | 2.84 | 0.07 | 0.68 | 0.05 | 78.37 | 0.00 | 0.64 |
| 2669 | 0.03 | 0.11 | 3.30 | 13.09 | 0.05 | 0.78 | 2.84 | 0.07 | 0.68 | 0.05 | 78.34 | 0.00 | 0.65 |
| 2696 | 0.03 | 0.11 | 3.29 | 13.07 | 0.05 | 0.78 | 2.83 | 0.08 | 0.68 | 0.05 | 78.38 | 0.00 | 0.64 |
| 2716 | 0.03 | 0.11 | 3.30 | 13.15 | 0.04 | 0.78 | 2.83 | 0.07 | 0.67 | 0.05 | 78.32 | 0.00 | 0.63 |
| 2740 | 0.03 | 0.11 | 3.30 | 13.11 | 0.05 | 0.80 | 2.83 | 0.07 | 0.69 | 0.05 | 78.33 | 0.00 | 0.63 |
| 2764 | 0.03 | 0.11 | 3.30 | 13.13 | 0.05 | 0.81 | 2.83 | 0.07 | 0.69 | 0.05 | 78.29 | 0.00 | 0.63 |
| 2788 | 0.03 | 0.12 | 3.30 | 13.11 | 0.05 | 0.80 | 2.84 | 0.07 | 0.69 | 0.05 | 78.31 | 0.00 | 0.63 |
| 2860 | 0.03 | 0.12 | 3.29 | 13.02 | 0.05 | 0.82 | 2.84 | 0.07 | 0.70 | 0.05 | 78.38 | 0.00 | 0.63 |

TABLE 10-continued

Course over time of the composition of the product mixture according to Example 8

| t [h] | 2-Methyl-butanal | n-Pentanal | 2-Me-1-Butanol | n-Pentanol | 4-Me-2-Pr-2-Hexenal | 4-Me-2-Pr-2-Hexanal | 4-Me-2-Pr-2-Hexenol | 4-Me-2-Pr-2-Hexanol | 2-Pr-2-Heptenal (1) unbr. | 2-Pr-2-Heptenal (2) br. | 2-PH-ol | 2-PHE-ol | Unknown |
|---|---|---|---|---|---|---|---|---|---|---|---|---|---|
| 2884 | 0.03 | 0.12 | 3.30 | 13.05 | 0.05 | 0.82 | 2.84 | 0.07 | 0.72 | 0.05 | 78.32 | 0.00 | 0.63 |
| 2908 | 0.03 | 0.12 | 3.30 | 13.12 | 0.05 | 0.82 | 2.83 | 0.07 | 0.71 | 0.05 | 78.26 | 0.00 | 0.63 |
| 2932 | 0.03 | 0.12 | 3.31 | 13.16 | 0.05 | 0.84 | 2.83 | 0.07 | 0.72 | 0.06 | 78.19 | 0.00 | 0.63 |
| 2956 | 0.03 | 0.12 | 3.30 | 13.13 | 0.05 | 0.83 | 2.84 | 0.07 | 0.72 | 0.05 | 78.24 | 0.00 | 0.62 |
| 3028 | 0.03 | 0.12 | 3.29 | 13.34 | 0.05 | 0.81 | 2.84 | 0.08 | 0.71 | 0.05 | 78.06 | 0.00 | 0.62 |
| 3076 | 0.03 | 0.12 | 3.29 | 13.43 | 0.04 | 0.83 | 2.84 | 0.07 | 0.72 | 0.06 | 77.87 | 0.06 | 0.64 |
| 3100 | 0.03 | 0.13 | 3.28 | 13.45 | 0.04 | 0.86 | 2.83 | 0.07 | 0.74 | 0.06 | 77.83 | 0.08 | 0.61 |
| 3124 | 0.03 | 0.13 | 3.28 | 13.45 | 0.04 | 0.88 | 2.83 | 0.07 | 0.77 | 0.06 | 77.75 | 0.08 | 0.63 |
| 3196 | 0.03 | 0.12 | 3.25 | 13.12 | 0.04 | 0.88 | 2.85 | 0.07 | 0.77 | 0.06 | 78.09 | 0.09 | 0.61 |
| 3220 | 0.03 | 0.13 | 3.25 | 13.13 | 0.04 | 0.88 | 2.85 | 0.07 | 0.78 | 0.06 | 78.10 | 0.09 | 0.59 |
| 3244 | 0.03 | 0.13 | 3.23 | 13.15 | 0.04 | 0.89 | 2.85 | 0.07 | 0.78 | 0.06 | 78.18 | 0.00 | 0.59 |
| 3268 | 0.03 | 0.13 | 3.23 | 13.17 | 0.05 | 0.91 | 2.86 | 0.07 | 0.79 | 0.06 | 78.03 | 0.09 | 0.58 |
| 3292 | 0.03 | 0.13 | 3.23 | 13.15 | 0.05 | 0.91 | 2.86 | 0.07 | 0.79 | 0.06 | 78.03 | 0.08 | 0.60 |
| 3364 | 0.03 | 0.08 | 3.10 | 7.81 | 0.05 | 0.94 | 3.06 | 0.06 | 0.85 | 0.06 | 83.23 | 0.08 | 0.64 |
| 3388 | 0.03 | 0.07 | 3.11 | 7.82 | 0.05 | 0.94 | 3.06 | 0.06 | 0.85 | 0.06 | 83.23 | 0.09 | 0.62 |
| 3412 | 0.03 | 0.09 | 3.11 | 8.89 | 0.05 | 0.94 | 3.02 | 0.06 | 0.85 | 0.06 | 82.19 | 0.08 | 0.62 |
| 3436 | 0.03 | 0.09 | 3.13 | 9.17 | 0.05 | 0.95 | 3.01 | 0.06 | 0.85 | 0.06 | 81.89 | 0.09 | 0.62 |
| 3555 | 0.03 | 0.11 | 3.16 | 11.17 | 0.05 | 0.96 | 2.91 | 0.07 | 0.85 | 0.06 | 80.00 | 0.00 | 0.62 |
| 3580 | 0.03 | 0.04 | 3.03 | 5.09 | 0.05 | 1.01 | 3.15 | 0.06 | 0.95 | 0.07 | 85.88 | 0.00 | 0.63 |
| 3604 | 0.03 | 0.04 | 3.01 | 4.17 | 0.05 | 1.00 | 3.18 | 0.05 | 0.93 | 0.07 | 86.82 | 0.00 | 0.65 |
| 3628 | 0.03 | 0.04 | 3.00 | 4.07 | 0.05 | 1.00 | 3.19 | 0.05 | 0.93 | 0.07 | 86.90 | 0.00 | 0.67 |
| 3700 | 0.04 | 0.17 | 3.27 | 15.95 | 0.05 | 0.96 | 2.76 | 0.08 | 0.84 | 0.06 | 75.18 | 0.08 | 0.57 |
| 3724 | 0.04 | 0.18 | 3.27 | 15.99 | 0.05 | 0.96 | 2.75 | 0.08 | 0.85 | 0.06 | 75.14 | 0.08 | 0.56 |
| 3748 | 0.04 | 0.12 | 3.19 | 12.16 | 0.05 | 1.00 | 2.90 | 0.07 | 0.90 | 0.07 | 78.84 | 0.08 | 0.58 |
| 3772 | 0.04 | 0.12 | 3.17 | 11.30 | 0.05 | 0.99 | 2.93 | 0.07 | 0.90 | 0.07 | 79.70 | 0.09 | 0.58 |
| 3796 | 0.04 | 0.12 | 3.16 | 11.22 | 0.05 | 1.00 | 2.93 | 0.07 | 0.90 | 0.07 | 79.77 | 0.09 | 0.59 |
| 3868 | 0.04 | 0.15 | 3.22 | 13.58 | 0.05 | 1.00 | 2.84 | 0.08 | 0.89 | 0.07 | 77.41 | 0.08 | 0.58 |
| 3892 | 0.04 | 0.15 | 3.22 | 13.60 | 0.05 | 1.00 | 2.84 | 0.08 | 0.90 | 0.07 | 77.41 | 0.09 | 0.57 |
| 4016 | 0.02 | 0.09 | 3.22 | 13.47 | 0.04 | 0.63 | 2.88 | 0.10 | 0.51 | 0.03 | 78.41 | 0.00 | 0.60 |

Example 9

Not According to the Invention

The experiment described in Example 8 was carried out analogously with the same starting material and under the same conditions. However, a chromium-containing catalyst was used as was also used for the experiments described in DE19842370A1. The course over time of the composition of the product mixture is shown in Table 11; the composition of the starting material mixture corresponds here to the table entry at time t=0.

TABLE 11

Course over time of the composition of the product mixture according to Example 9

| t [h] | 2-Methyl-butanal | n-Pentanal | 2-Me-1-Butanol | n-Pentanol | 4-Me-2-Pr-2-Hexenal | 4-Me-2-Pr-2-Hexanal | 4-Me-2-Pr-2-Hexenol | 4-Me-2-Pr-2-Hexanol | 2-Pr-2-Heptenal (1) linear | 2-Pr-2-Heptenal (2) branched | 2-PH-ol | 2-PHE-ol | Unknown |
|---|---|---|---|---|---|---|---|---|---|---|---|---|---|
| 0 | 1.64 | 13.15 | 0.01 | 0.16 | 1.91 | 1.00 | 0.00 | 0.00 | 0.00 | 81.66 | 0.00 | 0.00 | 0.47 |
| 18 | 0.02 | 0.13 | 1.71 | 13.23 | 0.05 | 0.71 | 1.71 | 0.09 | 0.75 | 0.07 | 80.96 | 0.08 | 0.49 |
| 26 | 0.01 | 0.11 | 1.72 | 13.31 | 0.05 | 0.71 | 1.71 | 0.09 | 0.58 | 0.05 | 81.10 | 0.05 | 0.51 |
| 42 | 0.02 | 0.13 | 1.71 | 13.32 | 0.05 | 0.72 | 1.71 | 0.09 | 0.71 | 0.06 | 80.92 | 0.00 | 0.56 |
| 50 | 0.01 | 0.10 | 1.72 | 13.35 | 0.04 | 0.73 | 1.71 | 0.09 | 0.54 | 0.04 | 81.08 | 0.00 | 0.57 |
| 66 | 0.02 | 0.11 | 1.72 | 13.33 | 0.04 | 0.75 | 1.71 | 0.09 | 0.60 | 0.05 | 80.99 | 0.00 | 0.58 |
| 73 | 0.01 | 0.11 | 1.72 | 13.34 | 0.04 | 0.76 | 1.71 | 0.09 | 0.53 | 0.04 | 81.06 | 0.00 | 0.59 |
| 138 | 0.02 | 0.11 | 1.72 | 13.33 | 0.01 | 0.82 | 1.71 | 0.09 | 0.58 | 0.04 | 80.95 | 0.00 | 0.63 |
| 146 | 0.02 | 0.11 | 1.71 | 13.32 | 0.04 | 0.82 | 1.71 | 0.09 | 0.57 | 0.04 | 80.96 | 0.00 | 0.59 |
| 163 | 0.02 | 0.11 | 1.72 | 13.41 | 0.01 | 0.83 | 1.71 | 0.09 | 0.57 | 0.04 | 80.86 | 0.00 | 0.63 |
| 170 | 0.02 | 0.12 | 1.72 | 13.42 | 0.01 | 0.84 | 1.71 | 0.09 | 0.59 | 0.04 | 80.83 | 0.00 | 0.62 |
| 187 | 0.02 | 0.12 | 1.72 | 13.44 | 0.04 | 0.86 | 1.71 | 0.09 | 0.59 | 0.04 | 80.80 | 0.00 | 0.58 |
| 194 | 0.02 | 0.12 | 1.72 | 13.41 | 0.04 | 0.86 | 1.71 | 0.08 | 0.68 | 0.06 | 80.72 | 0.00 | 0.58 |
| 210 | 0.02 | 0.12 | 1.72 | 13.42 | 0.03 | 0.87 | 1.71 | 0.08 | 0.61 | 0.05 | 80.79 | 0.00 | 0.58 |
| 217 | 0.02 | 0.11 | 1.72 | 13.43 | 0.04 | 0.87 | 1.71 | 0.08 | 0.59 | 0.05 | 80.80 | 0.00 | 0.59 |
| 238 | 0.02 | 0.12 | 1.71 | 13.40 | 0.03 | 0.87 | 1.71 | 0.08 | 0.61 | 0.05 | 80.81 | 0.00 | 0.59 |
| 242 | 0.02 | 0.12 | 1.72 | 13.42 | 0.04 | 0.88 | 1.71 | 0.08 | 0.60 | 0.05 | 80.78 | 0.00 | 0.59 |
| 306 | 0.02 | 0.12 | 1.72 | 13.44 | 0.03 | 0.92 | 1.70 | 0.08 | 0.64 | 0.05 | 80.70 | 0.00 | 0.58 |
| 331 | 0.02 | 0.13 | 1.70 | 12.49 | 0.04 | 1.07 | 1.72 | 0.10 | 0.75 | 0.05 | 81.31 | 0.05 | 0.57 |
| 338 | 0.02 | 0.13 | 1.70 | 12.56 | 0.04 | 1.07 | 1.72 | 0.09 | 0.74 | 0.05 | 81.28 | 0.04 | 0.56 |
| 354 | 0.02 | 0.13 | 1.71 | 12.62 | 0.04 | 1.07 | 1.72 | 0.08 | 0.73 | 0.05 | 81.24 | 0.04 | 0.55 |
| 361 | 0.02 | 0.13 | 1.70 | 12.64 | 0.04 | 1.08 | 1.72 | 0.08 | 0.72 | 0.05 | 81.23 | 0.04 | 0.55 |
| 379 | 0.02 | 0.14 | 1.72 | 13.77 | 0.04 | 1.08 | 1.69 | 0.08 | 0.71 | 0.05 | 80.16 | 0.00 | 0.54 |
| 385 | 0.02 | 0.14 | 1.72 | 13.89 | 0.04 | 1.08 | 1.69 | 0.13 | 0.71 | 0.05 | 79.95 | 0.04 | 0.54 |
| 450 | 0.02 | 0.15 | 1.72 | 14.07 | 0.04 | 1.11 | 1.68 | 0.08 | 0.70 | 0.05 | 79.85 | 0.00 | 0.53 |

TABLE 11-continued

Course over time of the composition of the product mixture according to Example 9

| t [h] | 2-Methyl-butanal | n-Pentanal | 2-Me-1-Butanol | n-Pentanol | 4-Me-2-Pr-2-Hexenal | 4-Me-2-Pr-2-Hexanal | 4-Me-2-Pr-Hexenol | 4-Me-2-Pr-Hexanol | 2-Pr-2-Heptenal (1) linear | 2-Pr-2-Heptenal (2) branched | 2-PH-ol | 2-PHE-ol | Unknown |
|---|---|---|---|---|---|---|---|---|---|---|---|---|---|
| 458 | 0.02 | 0.14 | 1.72 | 14.09 | 0.04 | 1.10 | 1.68 | 0.08 | 0.69 | 0.05 | 79.86 | 0.00 | 0.53 |
| 498 | 0.02 | 0.14 | 1.72 | 13.50 | 0.04 | 1.17 | 1.69 | 0.08 | 0.73 | 0.05 | 80.32 | 0.00 | 0.54 |
| 522 | 0.02 | 0.14 | 1.72 | 13.44 | 0.04 | 1.18 | 1.70 | 0.08 | 0.73 | 0.05 | 80.36 | 0.00 | 0.53 |
| 530 | 0.02 | 0.15 | 1.71 | 13.41 | 0.04 | 1.18 | 1.69 | 0.08 | 0.81 | 0.06 | 80.29 | 0.00 | 0.54 |
| 619 | 0.02 | 0.15 | 1.71 | 13.34 | 0.04 | 1.21 | 1.69 | 0.08 | 0.74 | 0.06 | 80.43 | 0.00 | 0.53 |
| 626 | 0.02 | 0.14 | 1.71 | 13.34 | 0.04 | 1.21 | 1.69 | 0.08 | 0.74 | 0.06 | 80.44 | 0.00 | 0.53 |
| 643 | 0.02 | 0.15 | 1.71 | 13.34 | 0.04 | 1.22 | 1.69 | 0.08 | 0.76 | 0.06 | 80.40 | 0.00 | 0.53 |
| 660 | 0.03 | 0.14 | 2.58 | 13.20 | 0.06 | 1.15 | 2.68 | 0.09 | 0.70 | 0.05 | 78.75 | 0.00 | 0.56 |
| 667 | 0.03 | 0.14 | 2.76 | 13.18 | 0.07 | 1.16 | 2.90 | 0.08 | 0.72 | 0.06 | 78.28 | 0.04 | 0.56 |
| 684 | 0.03 | 0.14 | 2.89 | 13.15 | 0.07 | 1.19 | 3.04 | 0.08 | 0.72 | 0.06 | 78.03 | 0.04 | 0.55 |
| 708 | 0.04 | 0.16 | 3.00 | 14.02 | 0.07 | 1.19 | 3.13 | 0.08 | 0.72 | 0.06 | 76.95 | 0.05 | 0.55 |
| 715 | 0.04 | 0.16 | 3.04 | 14.23 | 0.07 | 1.22 | 3.18 | 0.08 | 0.72 | 0.05 | 76.63 | 0.05 | 0.54 |
| 780 | 0.04 | 0.16 | 3.13 | 14.41 | 0.07 | 1.27 | 3.27 | 0.08 | 0.72 | 0.05 | 76.21 | 0.05 | 0.52 |
| 804 | 0.04 | 0.12 | 3.27 | 11.33 | 0.08 | 1.33 | 3.54 | 0.07 | 0.80 | 0.06 | 78.77 | 0.05 | 0.53 |
| 811 | 0.04 | 0.12 | 3.31 | 10.50 | 0.08 | 1.34 | 3.61 | 0.06 | 0.79 | 0.06 | 79.51 | 0.05 | 0.53 |
| 828 | 0.04 | 0.11 | 3.34 | 9.88 | 0.08 | 1.35 | 3.67 | 0.06 | 0.79 | 0.06 | 80.03 | 0.04 | 0.54 |
| 835 | 0.04 | 0.11 | 3.35 | 9.82 | 0.08 | 1.35 | 3.67 | 0.06 | 0.80 | 0.06 | 80.05 | 0.05 | 0.54 |
| 852 | 0.04 | 0.12 | 3.34 | 9.79 | 0.08 | 1.36 | 3.68 | 0.06 | 0.80 | 0.06 | 80.08 | 0.05 | 0.54 |
| 859 | 0.04 | 0.12 | 3.34 | 9.82 | 0.08 | 1.37 | 3.67 | 0.06 | 0.78 | 0.06 | 80.07 | 0.05 | 0.55 |
| 876 | 0.04 | 0.20 | 3.27 | 15.20 | 0.08 | 1.30 | 3.39 | 0.07 | 0.74 | 0.06 | 75.08 | 0.05 | 0.52 |
| 883 | 0.04 | 0.20 | 3.27 | 15.81 | 0.08 | 1.30 | 3.38 | 0.07 | 0.75 | 0.06 | 74.49 | 0.05 | 0.51 |
| 972 | 0.05 | 0.20 | 3.28 | 16.33 | 0.08 | 1.33 | 3.36 | 0.08 | 0.76 | 0.06 | 73.94 | 0.05 | 0.49 |
| 996 | 0.05 | 0.17 | 3.54 | 14.47 | 0.08 | 1.37 | 3.47 | 0.07 | 0.78 | 0.06 | 75.39 | 0.05 | 0.50 |
| 1004 | 0.05 | 0.17 | 3.62 | 13.86 | 0.08 | 1.38 | 3.50 | 0.07 | 0.77 | 0.06 | 75.89 | 0.05 | 0.50 |
| 1020 | 0.05 | 0.17 | 3.67 | 13.55 | 0.08 | 1.40 | 3.52 | 0.07 | 0.79 | 0.06 | 76.09 | 0.04 | 0.51 |
| 1116 | 0.05 | 0.17 | 3.72 | 13.05 | 0.08 | 1.44 | 3.54 | 0.07 | 0.80 | 0.06 | 76.45 | 0.06 | 0.50 |
| 1124 | 0.05 | 0.17 | 3.72 | 13.08 | 0.08 | 1.45 | 3.54 | 0.07 | 0.81 | 0.06 | 76.41 | 0.05 | 0.51 |
| 1140 | 0.05 | 0.18 | 3.67 | 13.42 | 0.08 | 1.44 | 3.52 | 0.07 | 0.82 | 0.06 | 76.13 | 0.05 | 0.50 |
| 1148 | 0.05 | 0.17 | 3.65 | 13.48 | 0.08 | 1.45 | 3.52 | 0.07 | 0.82 | 0.06 | 76.08 | 0.05 | 0.50 |
| 1164 | 0.05 | 0.17 | 3.71 | 13.16 | 0.08 | 1.48 | 3.54 | 0.07 | 0.80 | 0.06 | 76.33 | 0.05 | 0.50 |
| 1171 | 0.05 | 0.17 | 3.72 | 13.13 | 0.09 | 1.49 | 3.54 | 0.07 | 0.84 | 0.07 | 76.28 | 0.05 | 0.50 |
| 1188 | 0.06 | 0.17 | 3.72 | 13.08 | 0.09 | 1.50 | 3.54 | 0.07 | 0.82 | 0.06 | 76.34 | 0.05 | 0.50 |
| 1212 | 0.05 | 0.17 | 3.73 | 12.99 | 0.08 | 1.51 | 3.54 | 0.07 | 0.81 | 0.06 | 76.42 | 0.05 | 0.50 |
| 1219 | 0.05 | 0.17 | 3.74 | 12.99 | 0.08 | 1.52 | 3.55 | 0.07 | 0.82 | 0.06 | 76.41 | 0.05 | 0.50 |
| 1284 | 0.06 | 0.18 | 3.73 | 12.96 | 0.09 | 1.55 | 3.54 | 0.07 | 0.83 | 0.06 | 76.39 | 0.05 | 0.50 |
| 1292 | 0.05 | 0.17 | 3.74 | 12.97 | 0.08 | 1.53 | 3.54 | 0.07 | 0.81 | 0.06 | 76.42 | 0.05 | 0.50 |
| 1308 | 0.06 | 0.18 | 3.73 | 12.96 | 0.09 | 1.55 | 3.54 | 0.06 | 0.84 | 0.06 | 76.38 | 0.05 | 0.51 |
| 1315 | 0.06 | 0.18 | 3.73 | 12.87 | 0.09 | 1.55 | 3.54 | 0.07 | 0.84 | 0.06 | 76.46 | 0.05 | 0.50 |
| 1332 | 0.06 | 0.18 | 3.73 | 12.69 | 0.09 | 1.57 | 3.56 | 0.07 | 0.89 | 0.08 | 76.54 | 0.05 | 0.50 |
| 1339 | 0.06 | 0.17 | 3.74 | 12.70 | 0.09 | 1.58 | 3.56 | 0.06 | 0.83 | 0.06 | 76.60 | 0.05 | 0.50 |
| 1356 | 0.06 | 0.18 | 3.74 | 12.68 | 0.09 | 1.59 | 3.56 | 0.06 | 0.85 | 0.06 | 76.59 | 0.05 | 0.50 |
| 1363 | 0.06 | 0.17 | 3.73 | 12.66 | 0.09 | 1.58 | 3.56 | 0.06 | 0.82 | 0.06 | 76.65 | 0.05 | 0.50 |
| 1380 | 0.06 | 0.17 | 3.73 | 12.65 | 0.09 | 1.59 | 3.56 | 0.06 | 0.86 | 0.07 | 76.61 | 0.05 | 0.50 |
| 1452 | 0.05 | 0.18 | 3.57 | 12.95 | 0.08 | 1.61 | 3.07 | 0.08 | 0.86 | 0.07 | 76.88 | 0.05 | 0.57 |
| 1460 | 0.06 | 0.18 | 3.58 | 12.97 | 0.08 | 1.62 | 3.07 | 0.08 | 0.85 | 0.07 | 76.85 | 0.05 | 0.57 |
| 1476 | 0.06 | 0.18 | 3.57 | 12.95 | 0.08 | 1.61 | 3.06 | 0.08 | 0.87 | 0.07 | 76.85 | 0.05 | 0.56 |
| 1483 | 0.06 | 0.18 | 3.58 | 12.96 | 0.08 | 1.62 | 3.06 | 0.08 | 0.87 | 0.07 | 76.83 | 0.05 | 0.56 |
| 1500 | 0.06 | 0.18 | 3.57 | 12.96 | 0.08 | 1.63 | 3.06 | 0.08 | 0.87 | 0.07 | 76.84 | 0.05 | 0.55 |
| 1520 | 0.06 | 0.19 | 3.54 | 13.02 | 0.08 | 1.66 | 2.95 | 0.08 | 0.88 | 0.07 | 76.85 | 0.05 | 0.58 |
| 1528 | 0.06 | 0.19 | 3.53 | 13.03 | 0.08 | 1.66 | 2.93 | 0.08 | 0.89 | 0.07 | 76.84 | 0.05 | 0.58 |
| 1546 | 0.06 | 0.19 | 3.53 | 13.03 | 0.07 | 1.67 | 2.93 | 0.08 | 0.88 | 0.07 | 76.85 | 0.05 | 0.58 |
| 1616 | 0.06 | 0.19 | 3.51 | 13.12 | 0.08 | 1.70 | 2.86 | 0.09 | 0.90 | 0.06 | 76.80 | 0.06 | 0.58 |
| 1624 | 0.06 | 0.19 | 3.51 | 13.11 | 0.08 | 1.71 | 2.86 | 0.09 | 0.90 | 0.07 | 76.79 | 0.06 | 0.59 |
| 1640 | 0.06 | 0.20 | 3.50 | 13.10 | 0.08 | 1.72 | 2.86 | 0.09 | 0.92 | 0.07 | 76.77 | 0.06 | 0.58 |
| 1648 | 0.06 | 0.19 | 3.50 | 13.13 | 0.07 | 1.72 | 2.85 | 0.09 | 0.87 | 0.07 | 76.82 | 0.06 | 0.58 |
| 1665 | 0.06 | 0.20 | 3.50 | 13.18 | 0.07 | 1.72 | 2.83 | 0.08 | 0.91 | 0.07 | 76.73 | 0.05 | 0.59 |
| 1672 | 0.06 | 0.20 | 3.50 | 13.20 | 0.07 | 1.73 | 2.83 | 0.09 | 0.90 | 0.07 | 76.71 | 0.05 | 0.59 |
| 1688 | 0.06 | 0.20 | 3.50 | 13.19 | 0.08 | 1.74 | 2.82 | 0.09 | 0.92 | 0.07 | 76.69 | 0.06 | 0.59 |
| 1717 | 0.06 | 0.19 | 3.48 | 13.09 | 0.07 | 1.74 | 2.82 | 0.09 | 0.91 | 0.07 | 76.84 | 0.06 | 0.58 |
| 1724 | 0.06 | 0.20 | 3.49 | 13.12 | 0.08 | 1.75 | 2.82 | 0.09 | 0.95 | 0.09 | 76.71 | 0.05 | 0.59 |
| 1784 | 0.06 | 0.20 | 3.49 | 13.14 | 0.08 | 1.78 | 2.81 | 0.09 | 0.95 | 0.07 | 76.67 | 0.06 | 0.58 |
| 1808 | 0.06 | 0.20 | 3.49 | 13.09 | 0.08 | 1.79 | 2.81 | 0.09 | 0.95 | 0.07 | 76.73 | 0.06 | 0.58 |
| 1820 | 0.06 | 0.20 | 3.50 | 13.10 | 0.08 | 1.80 | 2.81 | 0.09 | 0.92 | 0.07 | 76.74 | 0.06 | 0.58 |
| 1832 | 0.06 | 0.21 | 3.49 | 13.08 | 0.08 | 1.81 | 2.81 | 0.09 | 0.97 | 0.07 | 76.70 | 0.06 | 0.58 |
| 1840 | 0.06 | 0.20 | 3.49 | 13.07 | 0.08 | 1.81 | 2.82 | 0.09 | 0.94 | 0.07 | 76.73 | 0.06 | 0.58 |
| 1856 | 0.06 | 0.20 | 3.49 | 13.07 | 0.08 | 1.82 | 2.80 | 0.08 | 0.94 | 0.07 | 76.74 | 0.06 | 0.58 |
| 1880 | 0.06 | 0.20 | 3.48 | 13.05 | 0.07 | 1.82 | 2.79 | 0.09 | 0.96 | 0.07 | 76.75 | 0.06 | 0.60 |
| 1891 | 0.06 | 0.21 | 3.48 | 13.05 | 0.08 | 1.82 | 2.80 | 0.09 | 0.99 | 0.08 | 76.71 | 0.07 | 0.57 |
| 1952 | 0.06 | 0.21 | 3.49 | 13.06 | 0.08 | 1.87 | 2.80 | 0.09 | 0.98 | 0.08 | 76.65 | 0.07 | 0.58 |
| 1981 | 0.06 | 0.21 | 3.48 | 13.05 | 0.08 | 1.88 | 2.80 | 0.09 | 0.99 | 0.08 | 76.65 | 0.06 | 0.57 |
| 1988 | 0.06 | 0.21 | 3.49 | 13.04 | 0.08 | 1.89 | 2.81 | 0.09 | 1.00 | 0.08 | 76.61 | 0.07 | 0.58 |
| 2001 | 0.06 | 0.21 | 3.47 | 12.99 | 0.08 | 1.88 | 2.78 | 0.09 | 0.99 | 0.08 | 76.72 | 0.07 | 0.58 |
| 2024 | 0.06 | 0.21 | 3.49 | 13.04 | 0.08 | 1.91 | 2.80 | 0.08 | 0.97 | 0.07 | 76.64 | 0.06 | 0.58 |
| 2048 | 0.06 | 0.21 | 3.47 | 13.01 | 0.08 | 1.92 | 2.80 | 0.09 | 1.01 | 0.08 | 76.62 | 0.07 | 0.57 |

TABLE 11-continued

Course over time of the composition of the product mixture according to Example 9

| t [h] | 2-Methyl-butanal | n-Pentanal | 2-Me-1-Butanol | n-Pentanol | 4-Me-2-Pr-2-Hexenal | 4-Me-2-Pr-2-Hexanal | 4-Me-2-Pr-Hexenol | 4-Me-2-Pr-Hexanol | 2-Pr-2-Heptenal (1) linear | 2-Pr-2-Heptenal (2) branched | 2-PH-ol | 2-PHE-ol | Unknown |
|---|---|---|---|---|---|---|---|---|---|---|---|---|---|
| 2120 | 0.06 | 0.22 | 3.48 | 13.05 | 0.08 | 1.96 | 2.80 | 0.09 | 1.04 | 0.08 | 76.52 | 0.07 | 0.57 |
| 2144 | 0.07 | 0.22 | 3.48 | 13.04 | 0.08 | 1.97 | 2.80 | 0.09 | 1.03 | 0.08 | 76.51 | 0.07 | 0.57 |
| 2168 | 0.06 | 0.21 | 3.47 | 13.17 | 0.08 | 1.89 | 2.83 | 0.09 | 0.99 | 0.08 | 76.49 | 0.07 | 0.57 |
| 2192 | 0.06 | 0.21 | 3.48 | 13.10 | 0.08 | 1.92 | 2.81 | 0.09 | 1.01 | 0.08 | 76.51 | 0.07 | 0.57 |
| 2216 | 0.06 | 0.21 | 3.47 | 13.00 | 0.08 | 1.93 | 2.80 | 0.09 | 1.00 | 0.08 | 76.61 | 0.07 | 0.58 |
| 2288 | 0.07 | 0.22 | 3.36 | 13.03 | 0.07 | 2.01 | 2.76 | 0.10 | 1.08 | 0.08 | 76.55 | 0.08 | 0.59 |
| 2312 | 0.06 | 0.22 | 3.36 | 13.04 | 0.09 | 2.01 | 2.77 | 0.10 | 1.06 | 0.07 | 76.55 | 0.07 | 0.60 |
| 2315 | 0.06 | 0.22 | 3.35 | 13.01 | 0.08 | 1.91 | 2.79 | 0.13 | 1.02 | 0.08 | 76.62 | 0.06 | 0.67 |
| 2331 | 0.06 | 0.22 | 3.32 | 13.04 | 0.08 | 2.01 | 2.76 | 0.10 | 1.05 | 0.08 | 76.59 | 0.07 | 0.61 |
| 2355 | 0.06 | 0.22 | 3.31 | 13.06 | 0.08 | 2.03 | 2.75 | 0.10 | 1.06 | 0.08 | 76.56 | 0.07 | 0.60 |
| 2379 | 0.06 | 0.22 | 3.31 | 13.05 | 0.08 | 2.03 | 2.75 | 0.10 | 1.07 | 0.09 | 76.51 | 0.07 | 0.64 |
| 2451 | 0.06 | 0.22 | 3.27 | 12.95 | 0.08 | 2.08 | 2.75 | 0.10 | 1.08 | 0.08 | 76.64 | 0.07 | 0.61 |
| 2475 | 0.07 | 0.23 | 3.28 | 12.96 | 0.08 | 2.10 | 2.75 | 0.10 | 1.08 | 0.08 | 76.60 | 0.07 | 0.61 |
| 2499 | 0.06 | 0.22 | 3.27 | 12.93 | 0.08 | 2.10 | 2.74 | 0.10 | 1.07 | 0.08 | 76.65 | 0.07 | 0.61 |
| 2523 | 0.07 | 0.23 | 3.26 | 12.89 | 0.09 | 2.12 | 2.74 | 0.10 | 1.09 | 0.08 | 76.65 | 0.07 | 0.61 |
| 2547 | 0.07 | 0.23 | 3.27 | 12.91 | 0.08 | 2.14 | 2.74 | 0.10 | 1.10 | 0.08 | 76.60 | 0.07 | 0.61 |
| 2619 | 0.07 | 0.23 | 3.26 | 12.97 | 0.08 | 2.16 | 2.73 | 0.10 | 1.10 | 0.08 | 76.54 | 0.08 | 0.61 |
| 2643 | 0.07 | 0.24 | 3.26 | 12.96 | 0.08 | 2.18 | 2.73 | 0.10 | 1.14 | 0.09 | 76.47 | 0.08 | 0.61 |
| 2667 | 0.07 | 0.24 | 3.25 | 12.97 | 0.09 | 2.20 | 2.73 | 0.10 | 1.14 | 0.09 | 76.43 | 0.08 | 0.61 |
| 2691 | 0.07 | 0.23 | 3.26 | 13.00 | 0.09 | 2.21 | 2.73 | 0.10 | 1.09 | 0.08 | 76.45 | 0.08 | 0.61 |
| 2716 | 0.07 | 0.24 | 3.26 | 12.98 | 0.08 | 2.23 | 2.73 | 0.10 | 1.15 | 0.09 | 76.39 | 0.08 | 0.61 |
| 2787 | 0.07 | 0.24 | 3.25 | 13.02 | 0.08 | 2.25 | 2.72 | 0.10 | 1.16 | 0.09 | 76.32 | 0.08 | 0.61 |
| 2811 | 0.07 | 0.25 | 3.26 | 13.02 | 0.08 | 2.26 | 2.73 | 0.10 | 1.16 | 0.09 | 76.31 | 0.08 | 0.61 |
| 2835 | 0.07 | 0.24 | 3.25 | 13.02 | 0.08 | 2.27 | 2.72 | 0.10 | 1.16 | 0.09 | 76.30 | 0.08 | 0.61 |
| 2859 | 0.07 | 0.25 | 3.26 | 13.04 | 0.08 | 2.29 | 2.72 | 0.10 | 1.17 | 0.09 | 76.24 | 0.08 | 0.61 |
| 2883 | 0.07 | 0.25 | 3.25 | 13.01 | 0.08 | 2.30 | 2.72 | 0.10 | 1.18 | 0.09 | 76.25 | 0.08 | 0.61 |
| 2955 | 0.07 | 0.25 | 3.25 | 13.06 | 0.08 | 2.32 | 2.71 | 0.10 | 1.22 | 0.09 | 76.14 | 0.09 | 0.61 |
| 2979 | 0.07 | 0.25 | 3.26 | 13.08 | 0.08 | 2.35 | 2.72 | 0.10 | 1.17 | 0.09 | 76.13 | 0.09 | 0.61 |
| 3003 | 0.07 | 0.25 | 3.25 | 13.06 | 0.08 | 2.36 | 2.71 | 0.10 | 1.19 | 0.09 | 76.14 | 0.09 | 0.61 |
| 3027 | 0.07 | 0.25 | 3.25 | 13.03 | 0.08 | 2.39 | 2.72 | 0.10 | 1.19 | 0.09 | 76.13 | 0.09 | 0.61 |
| 3051 | 0.07 | 0.26 | 3.23 | 12.99 | 0.08 | 2.38 | 2.71 | 0.11 | 1.22 | 0.10 | 76.15 | 0.09 | 0.60 |
| 3123 | 0.08 | 0.27 | 3.24 | 13.22 | 0.09 | 2.44 | 2.70 | 0.10 | 1.26 | 0.09 | 75.82 | 0.09 | 0.59 |
| 3171 | 0.07 | 0.27 | 3.23 | 13.29 | 0.09 | 2.44 | 2.71 | 0.10 | 1.25 | 0.09 | 75.74 | 0.14 | 0.58 |
| 3195 | 0.07 | 0.27 | 3.24 | 13.33 | 0.09 | 2.46 | 2.71 | 0.10 | 1.21 | 0.09 | 75.71 | 0.13 | 0.59 |
| 3218 | 0.07 | 0.27 | 3.23 | 13.32 | 0.09 | 2.47 | 2.70 | 0.10 | 1.26 | 0.09 | 75.65 | 0.14 | 0.59 |
| 3290 | 0.08 | 0.27 | 3.23 | 13.32 | 0.09 | 2.50 | 2.70 | 0.11 | 1.29 | 0.10 | 75.59 | 0.16 | 0.57 |
| 3314 | 0.07 | 0.27 | 3.21 | 13.23 | 0.09 | 2.53 | 2.71 | 0.10 | 1.26 | 0.09 | 75.70 | 0.14 | 0.59 |
| 3327 | 0.07 | 0.27 | 3.21 | 13.18 | 0.09 | 2.46 | 2.72 | 0.11 | 1.28 | 0.09 | 75.82 | 0.14 | 0.58 |
| 3349 | 0.08 | 0.27 | 3.19 | 13.11 | 0.09 | 2.51 | 2.73 | 0.11 | 1.28 | 0.09 | 75.83 | 0.14 | 0.58 |
| 3373 | 0.08 | 0.27 | 3.18 | 13.11 | 0.09 | 2.54 | 2.72 | 0.10 | 1.29 | 0.09 | 75.79 | 0.15 | 0.58 |
| 3445 | 0.07 | 0.18 | 3.09 | 9.04 | 0.10 | 2.68 | 2.86 | 0.08 | 1.36 | 0.10 | 79.68 | 0.15 | 0.60 |
| 3469 | 0.08 | 0.19 | 3.08 | 8.96 | 0.10 | 2.69 | 2.87 | 0.09 | 1.43 | 0.10 | 79.66 | 0.15 | 0.61 |
| 3493 | 0.08 | 0.44 | 3.25 | 16.40 | 0.09 | 2.43 | 2.60 | 0.11 | 1.19 | 0.09 | 72.47 | 0.15 | 0.72 |
| 3517 | 0.08 | 0.45 | 3.35 | 20.46 | 0.09 | 2.49 | 2.45 | 0.13 | 1.20 | 0.09 | 68.52 | 0.14 | 0.56 |
| 3637 | 0.01 | 0.44 | 3.31 | 18.83 | 0.09 | 2.67 | 2.50 | 0.13 | 1.31 | 0.09 | 69.89 | 0.15 | 0.56 |
| 3661 | 0.08 | 0.16 | 3.10 | 9.56 | 0.10 | 2.94 | 2.83 | 0.10 | 1.49 | 0.11 | 78.78 | 0.16 | 0.59 |
| 3685 | 0.08 | 0.15 | 3.03 | 6.83 | 0.11 | 2.98 | 2.94 | 0.08 | 1.56 | 0.11 | 81.36 | 0.14 | 0.62 |
| 3709 | 0.08 | 0.15 | 3.01 | 6.61 | 0.11 | 3.00 | 2.94 | 0.08 | 1.56 | 0.11 | 81.59 | 0.15 | 0.61 |
| 3781 | 0.09 | 0.45 | 3.30 | 18.89 | 0.10 | 2.80 | 2.48 | 0.13 | 1.34 | 0.10 | 69.60 | 0.16 | 0.57 |
| 3805 | 0.09 | 0.47 | 3.29 | 18.89 | 0.10 | 2.83 | 2.48 | 0.13 | 1.39 | 0.10 | 69.52 | 0.15 | 0.56 |
| 3829 | 0.09 | 0.39 | 3.24 | 16.82 | 0.10 | 2.92 | 2.55 | 0.12 | 1.44 | 0.10 | 71.50 | 0.16 | 0.56 |
| 3853 | 0.09 | 0.38 | 3.21 | 15.85 | 0.10 | 2.96 | 2.59 | 0.12 | 1.43 | 0.10 | 72.43 | 0.16 | 0.57 |
| 3877 | 0.09 | 0.39 | 3.21 | 15.76 | 0.11 | 3.00 | 2.59 | 0.12 | 1.50 | 0.11 | 72.40 | 0.16 | 0.57 |
| 3949 | 0.09 | 0.39 | 3.20 | 15.63 | 0.11 | 3.08 | 2.58 | 0.12 | 1.49 | 0.10 | 72.45 | 0.18 | 0.57 |
| 3973 | 0.10 | 0.40 | 3.20 | 15.60 | 0.11 | 3.13 | 2.59 | 0.13 | 1.51 | 0.11 | 72.38 | 0.17 | 0.58 |
| 3997 | 0.09 | 0.36 | 3.18 | 14.45 | 0.11 | 3.20 | 2.62 | 0.12 | 1.58 | 0.11 | 73.41 | 0.18 | 0.59 |
| 4117 | 0.10 | 0.37 | 3.15 | 13.73 | 0.12 | 3.43 | 2.63 | 0.11 | 1.65 | 0.11 | 73.82 | 0.19 | 0.58 |

CONCLUSION

The examples show that the catalyst prepared chromium-free is suitable for hydrogenating oxo aldehydes.

Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for the preparation of alcohols from aldehydes in a single catalytic hydrogenation reaction, comprising contacting a use mixture with a heterogeneous catalyst in the presence of hydrogen to produce a product mixture, wherein:
   a) said use mixture originates from a hydroformylation reaction and comprises a plurality of aldehydes with the same number, n, of carbon atoms, and corresponding alcohols and high boilers, where n is a natural number between three and eighteen;
   b) said use mixture comprises the following components adding up to 100% by weight:
      total fraction of the aldehydes having nine carbon atoms: 15% to 65% by weight;

total fraction of the alcohols having nine carbon atoms: 20% to 65% by weight;
total fraction of acetals: 0.5% to 5.5% by weight;
total fraction of other hydrocarbons: 0% to 40% by weight;
water: 0% to 1% by weight;
c) said product mixture comprises at least an alcohol corresponding to the hydrogenated aldehyde, and at least one by-product;
d) said catalyst comprises a support material comprising aluminium oxide or silicon dioxide or a mixture of aluminium oxide and silicon dioxide, with nickel and copper applied thereto, and which, in activated form, comprises the following composition adding up to 100% by weight:
support material: from 85% by weight to 95% by weight;
copper: from 5.3% by weight to 8.4% by weight;
nickel: from 2.2% by weight to 3.9% by weight;
chromium: less than 50 ppm by weight;
others: less than 1% by weight.

2. The process of claim 1, wherein the specific pore volume of the support material is between 0.5 ml/g to 0.9 ml/g, determined by the cyclohexane immersion method, and the specific surface area of the support material (BET surface area) is between 240 $m^2$/g to 280 $m^2$/g, determined by ISO method 9277.

3. The process of claim 1, wherein said process is carried out at a pressure of between $15*10^5$ Pa and $25*10^5$ Pa and at a temperature between 140° C. and 180° C., the pressure and temperature being selected such that use mixture and product mixture are present in a liquid phase.

4. The process of claim 3, wherein the hydrogen is present in a superstoichiometric amount, the concentration of the hydrogen being selected such that at least some of the hydrogen is present dissolved in the liquid phase.

5. The process of claim 2, wherein said process is carried out at a pressure of between $15*10^5$ Pa and $25*10^5$ Pa and at a temperature between 140° C. and 180° C., the pressure and temperature being selected such that use mixture and product mixture are present in a liquid phase.

6. The process of claim 5, wherein the hydrogen is present in a superstoichiometric amount, the concentration of the hydrogen being selected such that at least some of the hydrogen is present dissolved in the liquid phase.

7. The process of claim 1, wherein said catalyst comprises support material in an amount of from 88% by weight to 92% by weight.

8. The process of claim 1, wherein said catalyst comprises copper in an amount of from 6.5% by weight to 7.0% by weight.

9. The process of claim 1, wherein said catalyst comprises nickel in an amount of from 2.8% by weight to 3.3% by weight.

10. The process of claim 1, wherein said catalyst comprises less than 5 ppm by weight of chromium.

11. The process of claim 1, wherein the surface area of said support material is 240 $m^2$/g to 280 $m^2$/g as determined by ISO method 9277.

12. The process of claim 7, wherein said catalyst comprises copper in an amount of from 6.5% by weight to 7.0% by weight.

13. The process of claim 7, wherein said catalyst comprises nickel in an amount of from 2.8% by weight to 3.3% by weight.

14. The process of claim 7, wherein said catalyst comprises less than 5 ppm by weight of chromium.

15. The process of claim 7, wherein the surface area of said support material is 240 $m^2$/g to 280 $m^2$/g as determined by ISO method 9277.

16. The process of claim 12, wherein said catalyst comprises nickel in an amount of from 2.8% by weight to 3.3% by weight.

17. The process of claim 12, wherein said catalyst comprises less than 5 ppm by weight of chromium.

18. The process of claim 12, wherein the surface area of said support material is 240 $m^2$/g to 280 $m^2$/g as determined by ISO method 9277.

19. The process of claim 17, wherein said catalyst comprises less than 5 ppm by weight of chromium.

20. The process of claim 17, wherein the surface area of said support material is 240 $m^2$/g to 280 $m^2$/g as determined by ISO method 9277.

* * * * *